United States Patent [19]
Huitema et al.

[11] Patent Number: 5,507,773
[45] Date of Patent: Apr. 16, 1996

[54] CABLE-ACTUATED JAW ASSEMBLY FOR SURGICAL INSTRUMENTS

[75] Inventors: Thomas W. Huitema, Cincinnati; Warren P. Williamson, Loveland; Matthew Otten, Cincinnati; Kenneth S. Wales, Mason, all of Ohio; Mark Fogelberg, Wilsonville, Oreg.; James H. Chambers, Milford, Ohio

[73] Assignee: Ethicon Endo-Surgery, Cincinnati, Ohio

[21] Appl. No.: 198,939

[22] Filed: Feb. 18, 1994

[51] Int. Cl.$^6$ .................................... A61B 17/00
[52] U.S. Cl. .................... 606/207; 128/751; 606/174
[58] Field of Search .................. 606/51, 52, 205–211, 606/174, 167, 170; 128/751–755

[56] References Cited

U.S. PATENT DOCUMENTS

| | | |
|---|---|---|
| 4,483,562 | 11/1984 | Schoolman . |
| 4,566,620 | 1/1986 | Green et al. . |
| 4,610,383 | 9/1986 | Rothfuss et al. . |
| 4,728,020 | 3/1988 | Green et al. . |
| 4,869,414 | 9/1989 | Green et al. . |
| 4,872,456 | 10/1989 | Hasson . |
| 4,950,273 | 8/1990 | Briggs ................................ 606/174 |
| 5,137,198 | 8/1992 | Nobis et al. . |
| 5,171,256 | 12/1992 | Smith et al. ....................... 606/205 |
| 5,209,747 | 5/1993 | Knoepfler . |
| 5,312,023 | 5/1994 | Green et al. . |
| 5,342,381 | 8/1994 | Tidemand .......................... 606/52 |
| 5,383,888 | 1/1995 | Zvenyatsky et al. ............... 606/174 |

*Primary Examiner*—Stephen C. Pellegrino
*Assistant Examiner*—William W. Lewis
*Attorney, Agent, or Firm*—Paul A. Coletti

[57] ABSTRACT

A jaw assembly is provided with a pair of jaws which are closed with a flexible, tension member that is pulled by the operator of the instrument. In a preferred embodiment, one of the jaws is pivotally mounted in a slot to the other jaw. A cord, having a loop configuration, is attached to the pivoting jaw and can be pulled to pivot the jaw closed. A second cord can be provided to initially hold the proximal end of the pivoting jaw away from the other jaw until the distal ends of the jaws are closer together. In another embodiment, jaws can be closed in a parallel orientation by rotating two pulleys with threaded shafts engaged with the jaws.

28 Claims, 13 Drawing Sheets

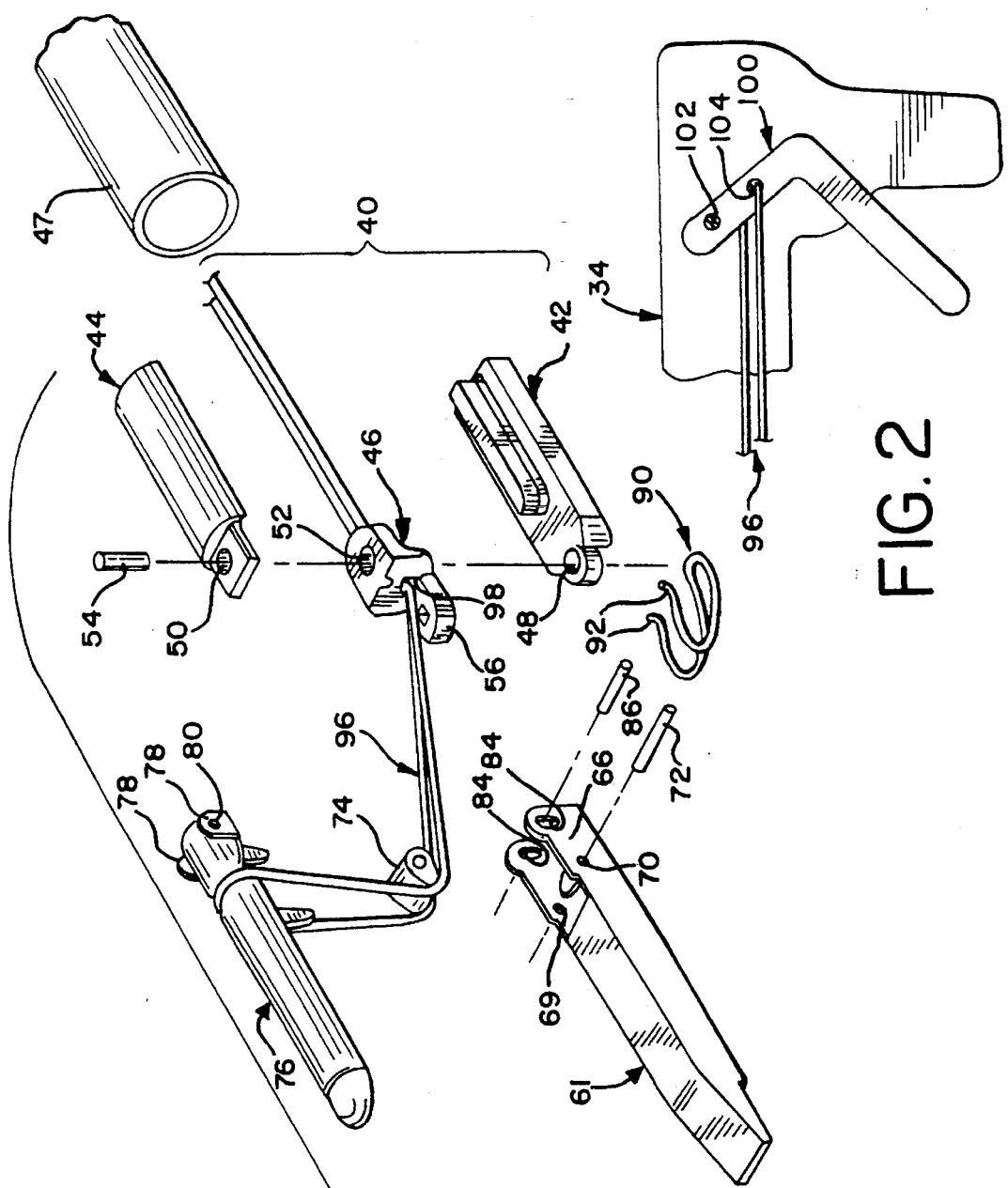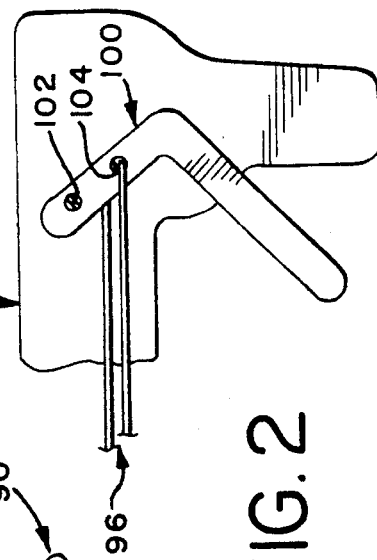

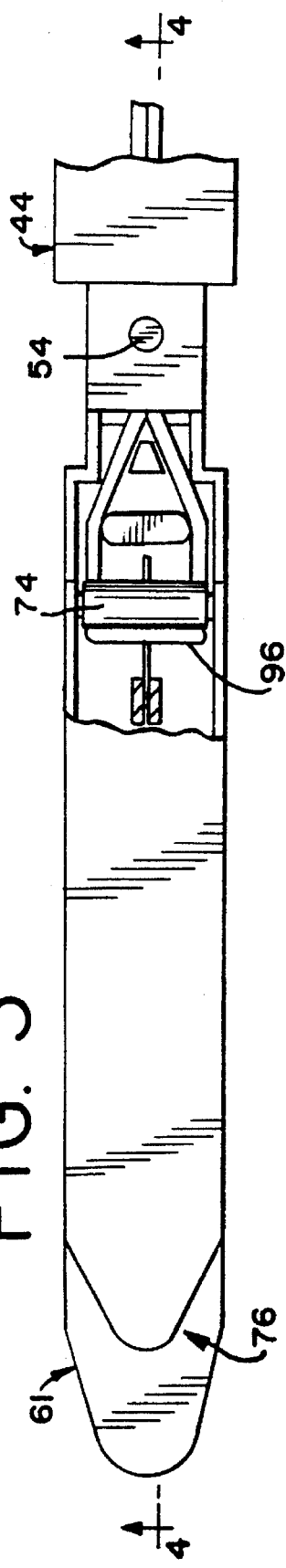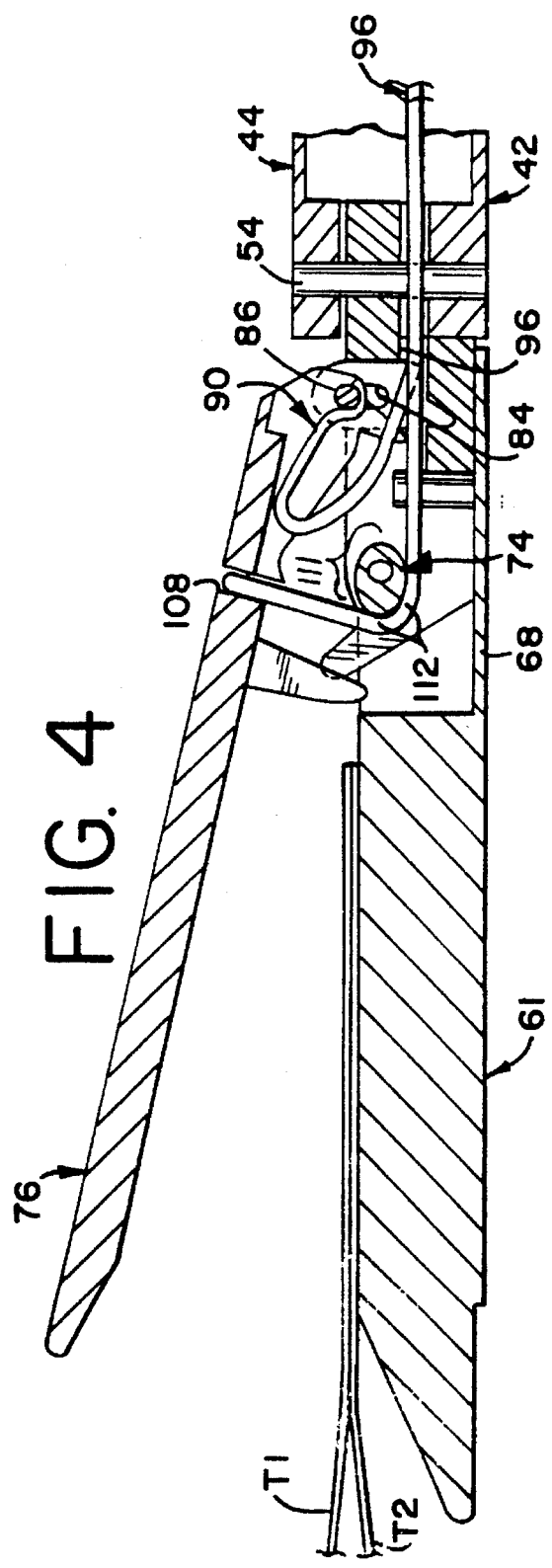

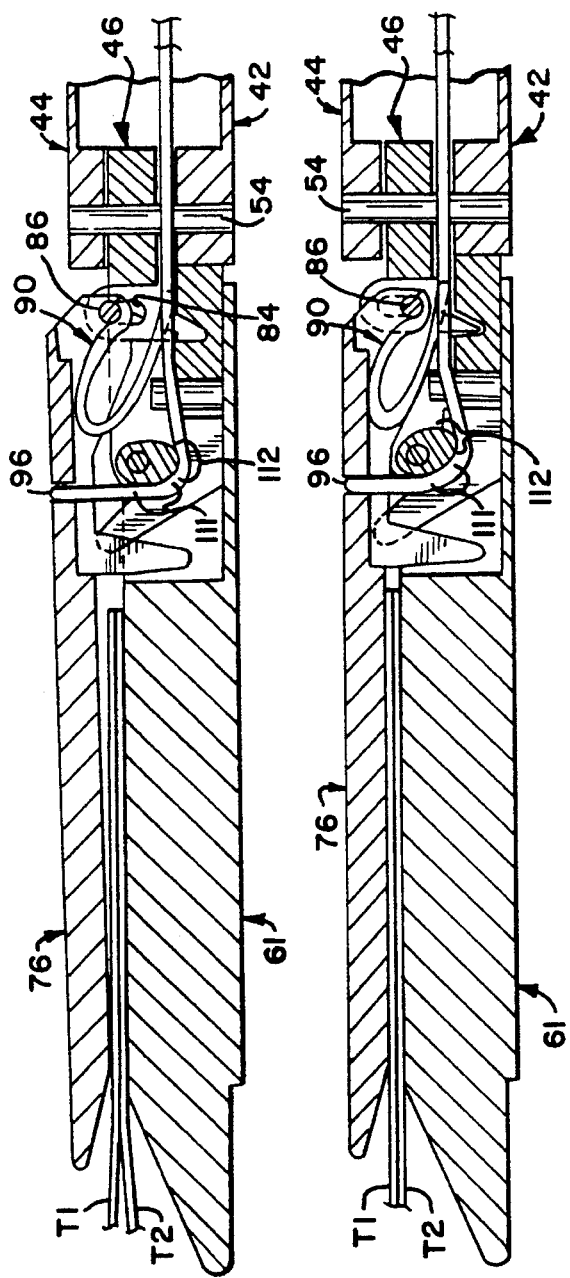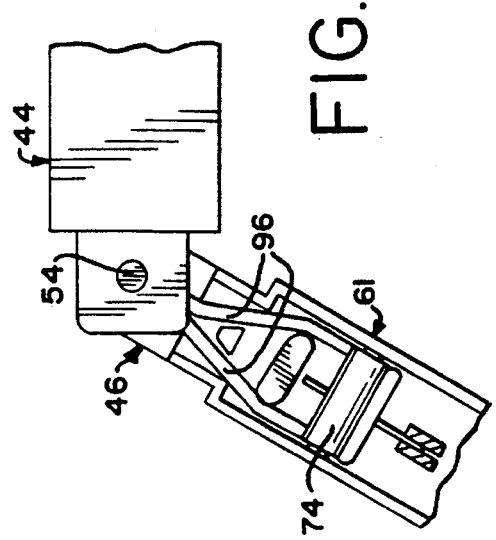

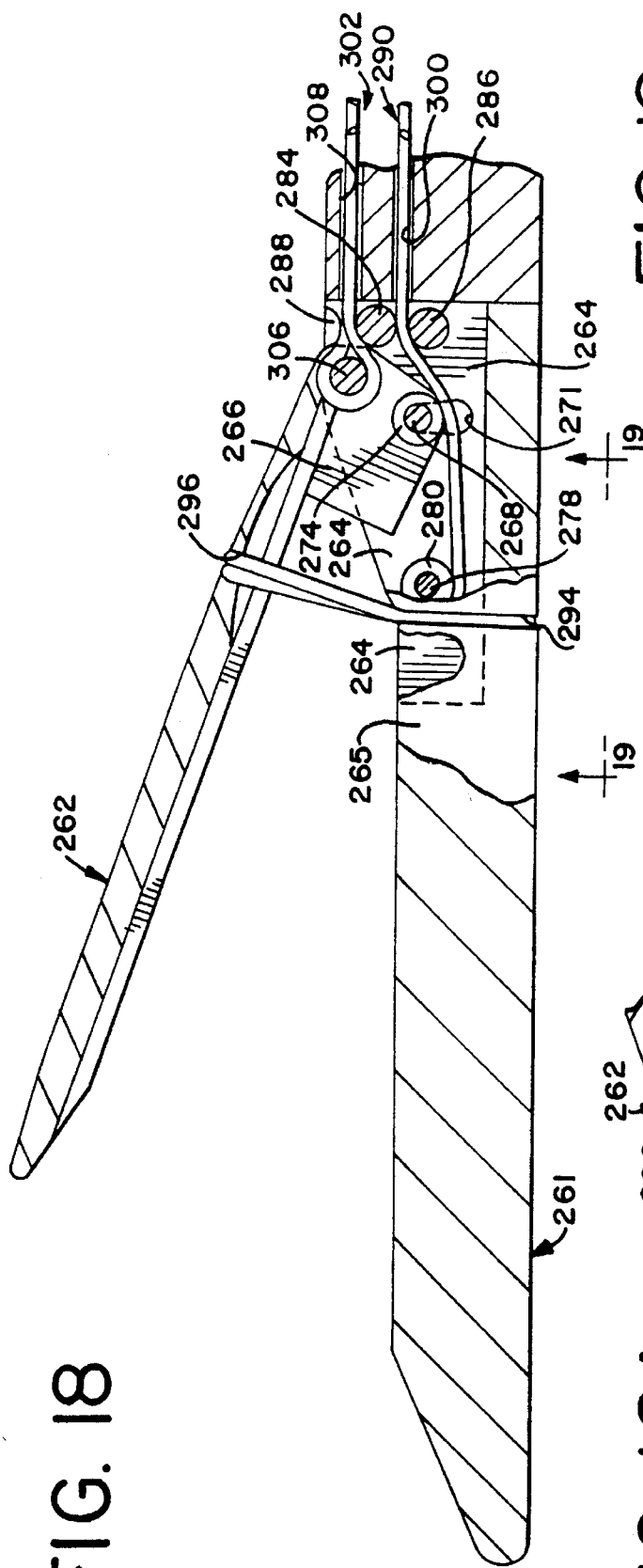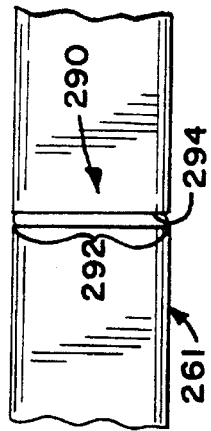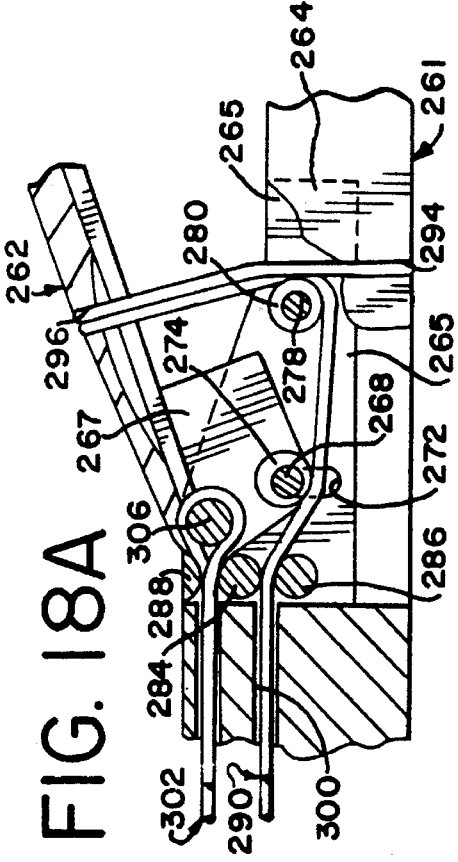

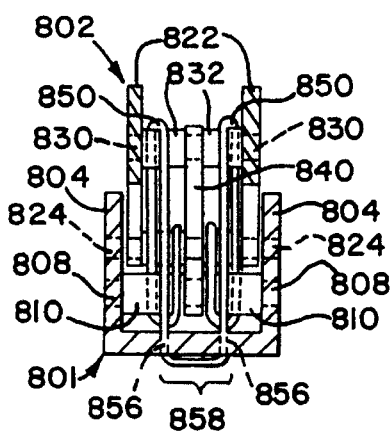
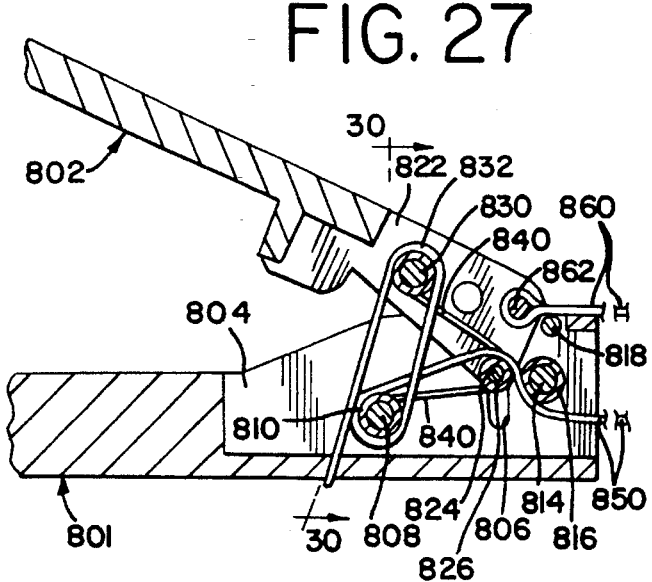
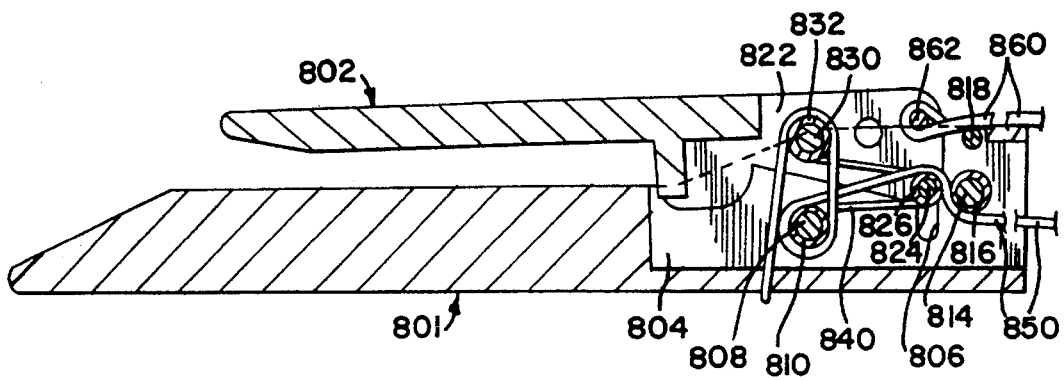
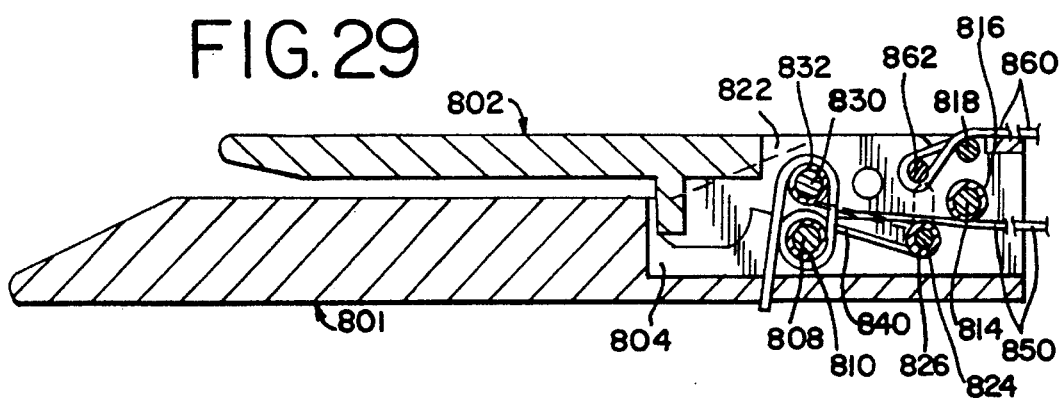

CABLE-ACTUATED JAW ASSEMBLY FOR SURGICAL INSTRUMENTS

TECHNICAL FIELD

This invention relates generally to surgical instruments and is especially suitable for incorporation in various instruments used in endoscopic procedures as well as in open surgery procedures.

BACKGROUND OF THE INVENTION AND TECHNICAL PROBLEMS POSED BY THE PRIOR ART

A variety of designs have been commercialized or proposed for instruments incorporating a pair of cooperating jaws (i.e., a jaw assembly) in which one jaw pivots or otherwise moves relative to the other jaw between open and closed positions. Examples of such instruments include tissue graspers, tissue clamps, needle graspers, tissue cutters, linear staplers, ligating clip appliers, and the like.

In many surgical procedures, the working area is confined, and instruments with relatively small cross sections are necessary or preferred. Thus, it would be desirable to provide an improved jaw assembly that can be incorporated in a surgical instrument and that has a relatively small cross section.

Some instrument designs have been developed for linear stapler systems wherein one jaw functions as an anvil and the other jaw carries a row or rows of staples. The anvil jaw can be closed manually to trap layers of tissue between the two jaws. Then, a suitable mechanism is actuated to discharge the staples through the tissue and against the anvil jaw. It would be beneficial to provide an improved jaw assembly design that could readily accommodate a staple application system and permit opening and closing of the jaws remotely from the proximal end of the instrument.

When pivotally-mounted jaws are employed to clamp or squeeze tissue, the proximal portions of the jaws typically engage the tissue before the distal portions of the jaws engage the tissue. This can cause the tissue to be forced distally in the jaws, and the tissue may then not be properly engaged by the jaws. It would be desirable to provide an improved jaw assembly that could close the jaws in a way that would eliminate or minimize the tendency of the tissue to move along the jaws as the jaws close.

In some surgical applications, it is necessary or advantageous to apply relatively high squeezing forces. Thus, it would be desirable to provide an improved jaw assembly that can provide a mechanical advantage for increasing the jaw closure force compared to the operator input force. It would also be beneficial if the jaw assembly could accommodate designs wherein the closure force at the jaw assembly can be varied during the closure stroke.

Additionally it would be advantageous to provide an improved jaw assembly that could be incorporated in instruments used in endoscopic surgical procedures as well as in instruments used in open surgery procedures. As used herein, the term "endoscopic" pertains generally to the use of a surgical instrument which is inserted into a body cavity in conjunction with an endoscope that is inserted into the same body cavity. The endoscope permits visual inspection, with or without magnification, of the interior of the body cavity and permits observation of the operation of the surgical instrument for therapeutic or diagnostic purposes.

In a typical endoscopic surgical procedure, the abdominal cavity of a human or animal subject is insufflated with a sterile gas, such as carbon dioxide, in order to provide increased maneuvering room within the body cavity for endoscopic instruments. Then, conventional trocars are inserted into the subject's body cavity through the surrounding skin, tissue, and musculature. A conventional trocar typically consists of a trocar cannula which houses an elongated trocar obturator. Trocar obturators typically have a piercing point, although other types of obturators are also available.

After each trocar has been positioned within the body cavity adjacent the target surgical site, the trocar obturator is removed leaving the trocar cannula as a pathway to the body cavity. A plurality of trocar cannulas are typically placed in this manner. The surgeon can then insert an endoscope through one of the trocar cannulas and can insert various types of endoscopic, surgical instruments through one or more of the other trocar cannulas at the target surgical site where the diagnostic or therapeutic surgical procedure is performed.

The endoscope is typically connected to a video camera, and the output from the video camera is fed to a video monitor which displays the surgical site and the end of the endoscopic instrument at the surgical site. Some endoscopic instruments incorporate a pair of jaws (e.g., ligating clip appliers, tissue cutters, tissue graspers, needle graspers, and the like). Thus, it would be desirable to provide an improved jaw assembly that can be employed in such endoscopic instruments and that can easily accommodate operation and control from the proximal end of the instrument exterior of the body cavity.

Although endoscopic surgical procedures offer many advantages, there are some problems associated with these procedures as conventionally practiced. For example, because the surgeon typically views the display on the video monitor as he manipulates instruments within the body cavity, the video display provides the surgeon with only a two-dimensional view of the surgical site, and there is a consequent loss of depth perception.

Another problem relates to engaging tissue from the instrument insertion direction. Some conventional, endoscopic instruments (e.g., graspers) include a jaw assembly for engaging the tissue in a way that effects the desired result (e.g., squeezing the tissue). In some of these conventional, endoscopic instruments, the jaws are mounted to, and extend generally linearly with, a rigid, straight shaft of the instrument.

Depending upon the nature of the operation to be performed on the tissue within the body cavity, it may be desirable to provide a jaw assembly which can be angled or articulated relative to the longitudinal axis of the instrument shaft. This can permit the surgeon to more easily engage the tissue in some situations.

A further problem relates to the potential for blocking part of the field of view with the endoscopic instrument. Thus, the use of an endoscopic instrument with an articulating distal end would permit the surgeon to engage the tissue with the jaws laterally offset relative to the instrument's main shaft. This would permit the engaged tissue and jaws to be better viewed through an adjacent endoscope with little or no interference from the main shaft.

Although a number of designs have been proposed for articulating endoscopic instruments, and although articulating endoscopes and other instruments are commercially available, it would be desirable to provide an improved design for a remotely operated jaw assembly that can accommodate articulation of the distal portion of the instrument to which the jaw assembly is mounted.

In particular, it would be advantageous to provide a jaw assembly for an articulating instrument (endoscopic or non-endoscopic) with the capability for jaw operation even when the assembly is oriented at a substantial oblique angle relative to the longitudinal axis of the instrument. Further, it would be beneficial if such an improved design permitted operation of the jaw assembly while the jaw assembly is articulated in any radial direction around the longitudinal axis of the instrument.

In endoscopic surgery it may be desirable in some situations to sense environmental characteristics at the surgical site (e.g., temperature, chemical, etc.). Further, it may be desirable to sense the actual presence or position of a component of the instrument. In addition, it may be beneficial to provide conduits for irrigation or aspiration at the surgical site. It may also be necessary to provide clips or staples at the site and to provide means, carried in the jaw assembly, for applying the clips or staples. Accordingly, it would be especially advantageous to provide an improved jaw assembly which can accommodate internal sensor lines, aspiration conduits, irrigation conduits, and flexible actuator members, and which can also accommodate the feeding and application of fasteners (e.g., of clips and staples). Such an improved jaw assembly should preferably have sufficient interior space that can accommodate internal passages and components and that can permit the movement of such components through the jaw assembly.

It would also be advantageous if such an improved jaw assembly for an endoscopic or open surgery instrument could be provided with a relatively smooth exterior configuration having a minimum of indentations and projections that might serve as sites for contaminants and be hard to clean or that might be more likely to catch on, or tear, adjacent tissue.

It would also be beneficial if such an improved jaw assembly could be provided with sufficient strength to accommodate relatively high moments and forces during operation of the instrument jaw assembly in an articulated orientation as well as in a straight orientation.

The present invention provides an improved jaw assembly for an instrument used in a surgical procedure which can accommodate designs having the above-discussed benefits and features.

SUMMARY OF THE INVENTION

According to the principles of the present invention, a unique jaw assembly is provided for a surgical instrument. The jaw assembly can be readily incorporated in an articulating instrument where the jaw assembly can be articulated relative to the rest of the instrument and can still be operated to open and close the jaws. The jaw assembly is relatively strong and can be operated to apply relatively high jaw closing forces.

The jaw assembly is readily operated from the proximal end of the instrument without requiring the application of excessively high input forces or torques.

Embodiments of the jaw assembly can be designed to provide a significant amount of internal clearance to accommodate components extending from the proximal end of the instrument through the jaw assembly. The internal region of the jaw assembly can also be designed to accommodate the passage of fasteners, such as ligating clips or staples.

The jaw assembly design can also be incorporated in embodiments wherein the tissue is compressed between substantially parallel jaws or between the distal ends of pivoting jaws so as to eliminate or minimize the movement of the tissue relative to the jaws when the jaws close.

The jaw assembly can be provided with a relatively smooth exterior configuration to minimize potential contamination sites or tissue snagging sites.

According to the teachings of the present invention, the jaw assembly includes a pair of jaws which are closed with a flexible, tension member that is pulled by the operator of the instrument. Such a flexible tension member may be a unitary or composite cord, cable, thin strip of metal or plastic, string, filament, or the like having a single strand or element as well as multiple strands or elements. Such a flexible, tension member transmits applied tension force but is typically ineffective to transmit any substantial compressive force. For convenience, the term "cord" is used throughout this specification and in the claims to broadly denote such a flexible, tension member.

In one form of the invention, a pair of jaws is provided in which one jaw is movable relative to the other. The jaws are actuated with an operating cord. The cord defines a loop having one portion operatively engaged with the movable jaw and another portion adapted to be engaged so as to apply tension to at least part of the loop to effect movement of the movable jaw. The use of an endless loop construction is especially advantageous with some types of cord materials wherein it is difficult to securely attach a cord end to instrument components because of cord brittleness or lubricity (e.g., liquid crystal materials or thermoplastic, polymer materials having a relatively low coefficient sliding friction).

In one embodiment of the invention, the assembly includes a first jaw having a distal end and a proximal end and includes a movable second jaw having a distal end and a proximal end. The second jaw is mounted for pivoting movement about a pivot axis toward and away from the first jaw. An operating cord is engaged with the second jaw distally of the pivot axis for pulling the second jaw to pivot the distal end of the second jaw toward the first jaw.

In some applications it is desirable to provide a second operating cord. The second operating cord is engaged with the second jaw and is arranged to pull the second jaw proximal end away from the first jaw when the second operating cord is tensioned. If the second operating cord is tensioned when the first operating cord is initially pulled, then the proximal end of the second jaw is initially held away from the first jaw so that the distal end of the second jaw moves toward the first jaw and engages the material between the jaws before the proximal end of the second jaw engages the material. This minimizes the tendency of the tissue to be moved distally along the jaws during the closure of the jaws.

In one preferred embodiment, the jaw assembly also includes a lever which has a lever pivot axis and which is mounted for pivoting movement about the lever pivot axis. The lever defines first and second surfaces for engaging the cord. The distance between the lever pivot axis and any part of the first surface is less than the distance between the lever pivot axis and any part of the second surface. When the cord is pulled, the lever pivots to change the length of the lever arm through which the cord acts. This assembly can be arranged so that the second jaw is first pulled by the cord with lower force through a longer range of movement and is subsequently pulled with higher force through a shorter range of movement.

In another embodiment, the jaw assembly also includes a first jaw having a distal end and a proximal end, as well as a movable second jaw having a distal end and a proximal end. One of the jaws defines an elongate slot adjacent its proximal end. The other jaw has a transversely extending shaft adjacent its proximal end and received in the slot for mounting the jaws together to accommodate translation and pivoting movement of the second jaw toward and away from the first jaw.

A spring is provided to bias the second jaw relative to the first jaw for urging the second jaw to pivot away from the first jaw.

A first operating cord is engaged with the second jaw at a first location distally of the shaft for pulling the second jaw to pivot the second jaw distal end toward the first jaw. The first operating cord is also engaged with the second jaw at a second location proximally of the first location for urging the second jaw proximal end away from the first jaw only during an initial portion of the pivoting movement of the second jaw distal end toward said first jaw. This permits the tissue to be initially engaged between the distal ends of the jaws so as to minimize the tendency of the tissue to be moved distally along the jaws during the closure of the jaws.

In another embodiment, the jaw assembly includes first and second jaws with at least one of the jaws being movable toward the other. A spring structure is provided for urging the jaws apart. The first jaw has a lateral guide surface. An operating cord defining a U-shaped loop configuration is engaged with the second jaw. The cord has at least one trailing portion extending around the lateral guide surface whereby the trailing portion can be pulled to urge at least one of the jaws toward the other of the jaws.

Another form of the jaw assembly includes a first jaw and a first guide surface fixed relative to the first jaw. A movable second jaw having a second guide surface is mounted for pivoting movement toward and away from the first jaw. A spring biases the second jaw relative to the first jaw for urging the second jaw to pivot away from the first jaw. A cord is provided with a portion fixed relative to the first jaw. The cord has a trailing portion trained sequentially from the fixed portion around the second guide surface and then around the first guide surface for pulling the second jaw to pivot toward the first jaw.

Another embodiment of the jaw assembly also has a first jaw with a distal end and a proximal end, as well as a movable second jaw having a distal end and a proximal end. One of the jaws defines an elongate slot adjacent its proximal end. The other jaw has a transversely extending shaft adjacent its proximal end and received in the slot for mounting the jaws together to accommodate translation and pivoting movement of the second jaw toward and away from the first jaw.

A spring biases the second jaw relative to the first jaw for urging the second jaw proximal end to translate away from the first jaw and to also urge the second jaw distal end to pivot away from the first jaw.

An operating cord is connected with the second jaw at a first location distally of the shaft for pulling the second jaw to pivot the second jaw distal end toward the first jaw. The operating cord is also engaged with the second jaw at a second location proximally of the first location for urging the second jaw proximal end toward the first jaw as the second jaw distal end moves toward the first jaw.

In another embodiment, the jaw assembly also includes a first jaw having a distal end and a proximal end as well as a movable second jaw provided with a distal end and a proximal end. One of the jaws defines an elongate slot adjacent its proximal end. The other jaw has a transversely extending shaft adjacent its proximal end and received in the slot for mounting the jaws together to accommodate translation and pivoting movement of the second jaw toward and away from the first jaw.

A first operating cord is engaged with the second jaw at a first location distally of the shaft for pulling the second jaw to pivot the second jaw distal end toward the first jaw. The first operating cord is also engaged with the second jaw at a second location proximally of the first location for urging the second jaw proximal end away from said first jaw only during an initial portion of the pivoting movement of the second jaw distal end toward the first jaw.

A second operating cord is engaged with the second jaw proximal end. Pulling the second cord urges the second jaw proximal end toward the first jaw with concomitant relative displacement between the shaft and slot.

In yet another embodiment, the jaw assembly includes a frame and a first jaw projecting transversely from the frame. A second jaw is carried on the frame for movement toward and away from the first jaw in an orientation fixed relative to the first jaw.

A first guide member is carried on either the first jaw or frame. A second guide member is carried on the second jaw. A slot is defined by either the frame or the second jaw. A pin is carried on the other of the frame and second jaw such that the pin is received in the slot to accommodate movement of the second jaw.

A spring biases the second jaw away from the first jaw. A cord is connected to the first jaw. The cord is trained sequentially from the first jaw around the second guide member and then around the first guide member. The cord extends from the first guide member proximally of the jaw assembly whereby the pulling of the cord effects the closure of the jaws.

A similar frame is also provided as part of yet another embodiment in which a first jaw projects transversely from the frame. A second jaw is carried on the frame for movement toward and away from the first jaw in an orientation fixed relative to the first jaw. A guide member is carried on either the first jaw or frame. A slot is defined by either the frame or second jaw. A pin is carried on the other of the frame and second jaw and is received in the slot to accommodate movement of the second jaw.

A spring biases the second jaw away from the first jaw. A cord is connected to the second jaw. The cord extends around the guide member and extends proximally of the jaw assembly whereby the pulling of said cord effects the closure of the jaws.

Another form of the jaw assembly includes at least a first rod having a first axial portion defining a right-hand thread and a second axial portion defining a left-hand thread. The assembly also includes a first jaw defining a first right-hand threaded bore for receiving and threadingly engaging the first rod first axial portion. The assembly further includes a second jaw defining a first left-hand threaded bore for receiving and threadingly engaging the first rod second axial portion. A cord is operatively associated with the first rod to apply torque to the rod and effect rotation of the rod when the cord is pulled. This causes the jaws to move toward or away from each other depending upon the direction of rotation of the rod.

The jaw assembly in another embodiment includes a first jaw having a distal end and a proximal end, and includes a movable second jaw having a distal end and a proximal end.

The second jaw is mounted for pivoting movement about a pivot axis toward and away from the first jaw. A roller is carried on the second jaw. A cord, which includes the distal end portion in the form of a flexible, metallic band, is engaged with the second jaw distally of the pivot axis and is trained around the roller. The band has a generally Z-shaped configuration. A spring can be provided in the jaw assembly to urge the second jaw to pivot and carry the distal end of the second jaw away from the first jaw. Pulling on the cord effects closure of the jaws.

Another embodiment of the jaw assembly is similar to the embodiment described immediately above. It differs in that the band is secured to the distal end of the second jaw, and a second roller is carried on the second jaw. A flexible, metallic band is trained around the first and second rollers.

Another embodiment of the jaw assembly includes a first jaw having a distal end and a proximal end, and a second jaw having a distal end and a proximal end. One of the jaws defines an elongate slot adjacent its proximal end, and the other jaw has a transversely extending shaft adjacent its proximal end. The shaft is received in the slot for mounting the jaws together to accommodate translation and pivoting movement of the second jaw toward and away from the first jaw. The first jaw has a first guide pin located distally of the slot and a second guide pin located proximally of the slot. The second jaw has a third guide pin located distally of the slot.

A spring biases the second jaw relative to the first jaw for urging the second jaw to pivot relative to the first jaw to an open position. The assembly also includes a first operating cord which has at least a first portion extending into the first jaw from the proximal end of the first jaw. The first cord first portion extends between, and engages, the first jaw second guide pin and the shaft in the slot. The first cord first portion extends distally from the shaft and sequentially around the first guide pin on the first jaw and then around the third guide pin on the second jaw. The first cord first portion extends from the third guide pin on the second jaw to, and is engaged with, the first jaw at a location spaced from the first guide pin.

A second operating cord is connected to the proximal end of the second jaw to assist in operating the second jaw. It can be pulled at the proper time during the pulling of the first cord. The tension on the second cord initially holds the proximal end of the second jaw away from the first jaw so that the distal end of the second jaw closes first.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a simplified, exploded, perspective view of the distal end of portion of an instrument which includes a first embodiment of the jaw assembly of the present invention;

FIG. 2 is a simplified, schematic representation of the proximal portion of the instrument showing the handle and a lever for operating the jaws;

FIG. 3 is a fragmentary, top plan view of the jaw assembly illustrated in FIG. 1, but FIG. 3 shows the jaw assembly in an open position with portions of the upper or second jaw cut away to illustrate interior detail;

FIG. 4 is a fragmentary, cross-sectional view taken generally along the plane 4—4 in FIG. 3;

FIG. 5 is a view similar to FIG. 4, but FIG. 4 shows a partially closed condition of the jaw assembly;

FIG. 6 is a view similar to FIG. 5 but shows a completely closed condition of the jaw assembly;

FIG. 7 is a fragmentary view similar to FIG. 3 and shows the jaw assembly in an articulated position at an oblique angle relative to the instrument longitudinal axis;

FIG. 18 is a fragmentary, cross-sectional view of a seventh embodiment of a jaw assembly;

FIG. 18A is a fragmentary view similar to FIG. 18, but FIG. 18A shows the side of the jaw assembly opposite from that visible in FIG. 18;

FIG. 19 is a fragmentary, bottom view of the jaw assembly taken generally along the plane 19—19 in FIG. 18;

FIG. 27 is a fragmentary, perspective view of a thirteenth embodiment of a jaw assembly;

FIG. 28 is a view similar to FIG. 27, but FIG. 28 shows the jaw assembly partially closed;

FIG. 29 is a view similar to FIG. 28, but FIG. 29 shows the jaw assembly in the fully closed condition; and FIG. 30 is a cross-sectional view taken generally along the plane 30—30 in FIG. 27.

DESCRIPTION OF THE PREFERRED EMBODIMENTS

Figure 8:
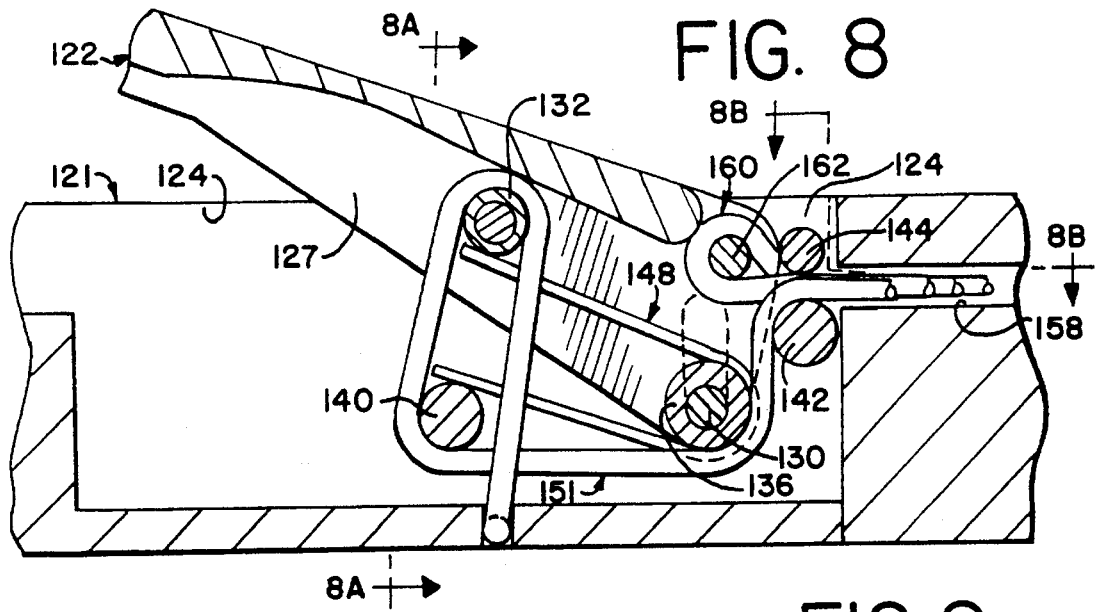
FIG. 8 is a fragmentary, cross-sectional view of a second embodiment of a jaw assembly in an open position.

One aspect of the present invention relates to a jaw assembly which can be incorporated in a variety of designs providing unique operational characteristics and capabilities. In particular, the jaw assembly is readily adapted for use at the distal end of an instrument which can be articulated. The jaw assembly is operable during and after articulation.

Further, some embodiments of the jaw assembly provide a mechanical advantage for increasing jaw force. In addition, some embodiments of the jaw assembly effect closure of the jaws by moving the jaws in a continuously parallel orientation. Other embodiments effect closure by moving the distal end of one of the jaws to a closed location before the proximal portion of the jaw is fully moved to a closed location. This minimizes the movement of tissue along the jaws during the jaw closing process.

The jaw assembly is relatively strong and can be provided with an exterior configuration that minimizes structural projections that might snag on tissue or accumulate contaminants.

In addition, the jaw assembly can be employed in instruments with devices for effecting a variety of functions with respect to the surgical site. Such functions can include, but are not limited to, grasping, clamping, applying staples or ligating clips, applying ultrasonic energy, irrigating the surgical site, or removing material from the site by aspiration or suction.

Various embodiments can be provided with sufficient interior space to accommodate internal passages and components (e.g., sensor lines, conduits, fastener actuation systems, etc.). Components for various sensor systems can be routed through the novel jaw assembly. Such sensor systems can include, but are not limited to, systems for measuring tissue thickness or compression, tumor sensing, pulse oximetry, and dopplar effect sensing of fluid in vessels. Also, light guides and other fiber optic system components may be routed through the assembly.

Further, the jaw assembly of the present invention accommodates various designs for venting or sealing the instrument in which the jaw assembly is incorporated, and the jaw assembly design accommodates the use of filters for filtering gas and smoke.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the jaw assembly embodiments of this invention are described in various operating positions, and terms such as upper, lower, horizontal, etc., are used with reference to these positions. It will be understood, however, that jaw assemblies incorporating this invention may be manufactured, stored, transported, used, and sold in an orientation other than the position described.

Figures illustrating the jaw assemblies show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

The jaw assemblies incorporating the present invention can be used in instruments that have certain conventional components the details of which, although not fully illustrated or described, will be apparent to those having skill in the art and an understanding of the necessary functions of such components.

FIGS. 1–7 schematically illustrate some basic features of a first embodiment of the jaw assembly of the present invention. The jaw assembly is adapted to be mounted to a proximal portion of an open surgery or endoscopic instrument, and the proximal portion may typically be a support housing 34 (FIG. 2). This part of the instrument is grasped by the surgeon. In an endoscopic instrument, the proximal part of the housing 34 remains outside of the patient while the rest of the instrument is inserted through the trocar cannula (not illustrated) and into the body cavity.

The jaw assembly can be pivotally mounted to the instrument, and to this end the instrument includes a mounting assembly 40 (FIG. 1) comprising a bottom bracket 42, a top bracket 44, and a support member 46. The lower bracket defines a bore 48, the upper bracket 44 defines a bore 50, and the support member 46 defines a bore 52. The components are assembled so that the bores 48, 52, and 50 are aligned to receive a hinge pin or pivot pin 54 (FIGS. 1 and 4). The proximal portions of the lower bracket 42 and upper bracket 44 are adapted to be mounted in a shaft tube 47 extending from the housing 34 by suitable means (not illustrated).

The support member 46 defines a cantilevered tongue 56 on which the jaw assembly is mounted. To this end, the jaw assembly includes a first or lower jaw 61 having a proximal portion in the form of a channel defined by a first side wall 64 (FIG. 1), a second side wall 66 (FIG. 1), and a bottom wall or floor 68 (FIG. 4). The projecting tongue 56 of the support member 46 is received within the proximal portion of the first jaw 61 as shown in FIG. 4 and is retained therein by suitable means (e.g., threaded fasteners, press fit, adhesive, welding or brazing, and the like (not illustrated)). The particular means by which the jaw assembly is attached to the tongue 56 or to any other portion of an instrument as may be desired, forms no part of the present invention.

The first jaw side wall 64 defines an aperture 69, and the first jaw side wall 66 defines an aperture 70. An oval lever arm 74 is disposed on a pin 72 which is mounted in the apertures 69 and 70 in the first jaw 61.

The jaw assembly includes an upper or second jaw 76 which has a proximal end portion defining a pair of bosses or ears 78. Each boss 78 defines a bore 80. The proximal portion of the second jaw 76 is received between the first jaw side walls 64 and 66. Each side wall 64 and 66 defines a vertically oriented, elongate slot 84. A shaft 86 is mounted through the slots 84 and through the second jaw bores 80 so as to retain the second jaw 76 mounted on the first jaw 61.

The length of each slot 84 is greater than the diameter of the shaft 86. The shaft 86 is thus free to translate vertically within the slots 84. This accommodates movement of the proximal portion of the second jaw 76 toward and away from the first jaw 61. Further, the shaft 86 may be characterized as defining a pivot axis about which the second jaw 76 can pivot. This pivot axis is, of course, not fixed and can translate relative to the first jaw 61 as the shaft 86 moves along the slots 84.

In the preferred embodiment illustrated, a spring 90 is mounted within the jaw assembly as illustrated in FIGS. 1 and 4. The spring 90 has a generally U-shaped configuration with the legs of the U bent over to define cradle portions 92 which engage the shaft 84 so as to bias the shaft, and hence the proximal end of the second jaw 76, upwardly away from the first jaw 61.

A cord 96 is provided for operating the jaw assembly to close the jaws. As discussed in greater detail under the section entitled "SUMMARY OF THE INVENTION," the term "cord" is used herein to refer generally to a flexible, tension member such as a cable, string, filament, thin strip of metal or plastic, or the like. The cord 96 may be a unitary or composite structure having a single strand or element. The cord 96 may also incorporate multiple strands or elements. Such structures and compositions may also be employed in cords used in the other jaw assembly embodiments described in detail hereinafter.

In the presently contemplated preferred embodiment, the cord 96 is a single loop of liquid crystal, polymer material having a relatively low coefficient of sliding friction. By using a continuous loop of the material, it is not necessary to attach or terminate a single end of the cord 96 to a component in the instrument. This is advantageous in the case of some types of cord materials wherein it is difficult to securely attach a cord end to instrument components. Such a loop structure may also be employed with cords used in other jaw assembly embodiments described in detail hereinafter.

The cord 96 defines a generally U-shaped configuration around the second jaw 76 and extends from the second jaw 76 around the lever 74. The cord 96 extends from the lever 74 beyond the proximal end of the jaw assembly where it may be pulled by a suitable means. In the embodiment illustrated in FIGS. 1–7, the instrument support member 46 defines an aperture 98 through which the cord 96 can extend proximally from the jaws 61 and 76. The cord 96 preferably extends to a proximal portion of the instrument, such as to the proximal end of the housing 34 (FIG. 2) where it can be pulled by the surgeon.

A presently preferred system for pulling the cord 96 is illustrated in FIG. 2 and comprises an L-shaped lever 100 pivotally mounted with a pin 102 to the housing 34. The loop of cord 96 extends through an aperture 104 in the operating lever 100. Because the spring 90 normally biases the second jaw 76 to the open position, the cord 96 is normally pulled distally so as to pull the operating lever 100 to a forward position against some suitable stop (not illustrated) in the housing 34. The surgeon can hold the proximal end of the housing 34 and squeeze the lever 100 rearwardly to pull the loop cord 96 proximally.

The distal end of the loop defined by the cord 96 is engaged with the second jaw 76. To this end, the outer surface of the second jaw 76 defines an arcuate groove 108 (FIG. 4) in which the cord 96 is seated. The cord 96 extends down both sides of the second jaw 76 into the channel section of the first jaw 61. The cord 96 is trained around, and engaged with, the exterior surface of the oval lever 74.

The lever 74 need not necessarily be oval but should have a first surface 111 and a second surface 112 (FIG. 4) wherein the distance between the lever pivot axis and any part of the first surface 111 is less than the distance between lever pivot axis and any part of the second surface 112. Preferably, the lever 74 is initially installed and engaged with the cord 96 such that the lever 74 has the orientation shown in FIG. 4 when the second jaw 76 is fully open. In particular, in this condition, the longest portion of the lever 74 (e.g., the major axis of an oval-shaped lever) is oriented generally parallel to the lower jaw 61 and is generally parallel to the length of the instrument along which the proximal portion of the loop of cord 96 is pulled. The cord 96 extending between the lever 74 and the second jaw 76 defines an angle of almost 90° with respect to the length of cord 96 extending proximally from the lever 74.

When the cord 96 is pulled proximally, the length of cord along the first surface 111 applies tension through a relatively short lever arm while the portion of the cord along the second surface 112 applies tension through a relatively long lever arm. As the cord 96 is pulled proximally, the lever 74 pivots (counterclockwise as viewed in FIG. 4). As the lever pivots to the intermediate position illustrated in FIG. 5, the length of cord 96 between the lever 74 and second jaw 76 is subjected to a relatively long travel at a relatively lower force. As the cord 96 continues to be pulled proximally from the orientation illustrated in FIG. 5 to the orientation illustrated in FIG. 6, the portion of the cord 96 engaged with the first surface 112 applies tension through a relatively long lever arm while the portion of the cord extending from the lever arm 74 to the second jaw 76 is tensioned through a relatively short lever arm. Thus, the travel of the cord 96 adjacent the second surface 112 is translated into a shorter travel and is subjected to a higher force.

The effect of the operation of the jaw assembly is to initially move the second jaw 76 through a relatively large percentage of the distance toward the closed position at relatively low force and to subsequently pivot the second jaw 76 through a short, remaining arc to the fully closed position at a relatively high force. For example, if the lever 74 is elliptical, and if the length of the major axis is equal to twice the length of the minor axis, then the second jaw 76 will be initially pulled toward the fully closed position with a force equal to ½ of the input pulling force and will pivot through an arc (as measured at the radius where the cord 96 engages the top of the second jaw 76) having a length equal to twice the initial pulling stroke length. Subsequently, when the lever 76 has pivoted about 90° (to the position illustrated in FIG. 5), the second jaw 76 will apply a clamping force equal to twice the pulling force as the second jaw 76 moves through an arc length equal to ½ of the final pull stroke length.

With reference to FIG. 4 and 5, it will be appreciated that during an initial pivoting movement of the second jaw 76, the proximal end of the second jaw 76 remains substantially elevated because the spring 90 is biasing the shaft 86 upwardly in the slots 84. Thus, as illustrated in FIG. 5, the distal end of the second jaw 76 initially engages material (e.g., two layers of tissue T1 and T2) before the more proximal portions of the jaw 76 can engage the material. This tends to initially clamp the material between the distal ends of the two jaws and eliminate or minimize the normal tendency of material to move along conventional jaws which pivot closed about a fixed pivot axis.

After the distal portion of the second jaw 76 has been pivoted to the substantially closed position, further force exerted by the pulling cord 96 is sufficient to overcome the force of the spring 90, and the proximal end of the second jaw 76 is pulled toward the first jaw 61 until the jaw assembly is completely closed as illustrated in FIG. 6.

The jaw assembly illustrated in FIGS. 1–7 can be used in an articulating surgical instrument. Because the jaw assembly is mounted, via the first jaw 61, to the tongue 56 of the pivotal support member 46, the jaw assembly moves with the support member 46 as it pivots about the axis defined by the pin 54. An articulated orientation of the jaw assembly on the support member 46 is illustrated in FIG. 7. The support member 46 can be pivoted relative to the brackets 42 and 44 in which it is mounted by any suitable means. For example, a pulley (not illustrated) can be fixed to the support member 46, and a drive belt or cord can be trained around the pulley. The drive belt or cord can be driven from the proximal end of the instrument by suitable means, such as a manually operated knob, motor, or other appropriate device. The particular mechanism or system for effecting pivoting of the support member 46 forms no part of the present invention.

The first jaw 61 and second jaw 76 are shown as having generally solid distal end portions. It will be appreciated that one or both of the jaws may have other configurations and may include hollow portions. Indeed, one or both of the jaws may include auxiliary components for acting on the tissue that is adjacent or clamped between the jaws. For example, one or both of the jaws could incorporate sensor lines, aspiration conduits, irrigation conduits, and the like.

Further, the jaws may be adapted to apply tissue fasteners, such as clips or staples. For example, the first jaw 61 may be provided with a staple cartridge having a row or rows of staples, and the second jaw 76 may incorporate an anvil design so that both jaws can function as a linear stapler. A suitable mechanism can be provided in the staple-carrying jaw to discharge the staples through the tissue against the anvil jaw. Such a mechanism could be operated by means of an actuating member extending from the proximal end of the instrument into the staple-carrying jaw. Linear stapler designs which may be suitable for adaptation and incorporation into the jaw assembly of the present invention are illustrated in the U.S. Pat. No. 4,610,383.

In the jaw assembly first embodiment described above, as well as in the other embodiments described hereinafter, the particular design of the portion of each jaw that engages the tissue and/or that contains auxiliary components of the type described above forms no part of the present invention. Further, it will be appreciated that the entire jaw assembly can be mounted in a fixed, as well as pivotable, arrangement to the distal end of an instrument (not shown). In this embodiment, as well as in other embodiments described hereinafter, the particular design of the structure for mounting the jaw assembly to the instrument forms no part of the present invention.

Another embodiment of the jaw assembly of the present invention is illustrated in FIGS. 8, 8A, 8B, 9, and 10. The jaw assembly has a first jaw 121 and a second jaw 122. Each jaw has a distal end and a proximal end. The jaws 121 and 122 are mounted together at their proximal ends.

Figure 9:
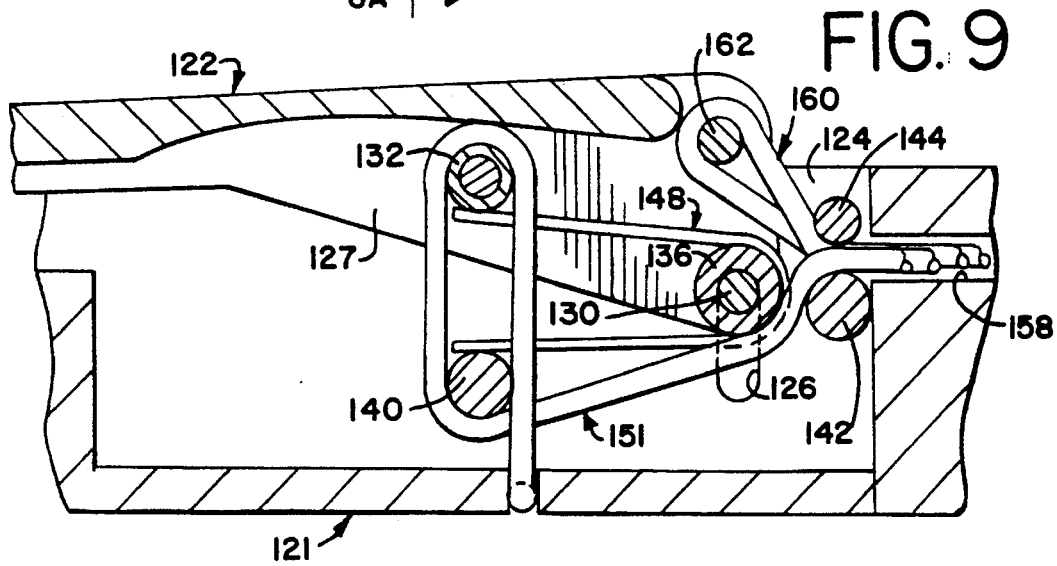
FIG. 9 is a view similar to FIG. 8, but FIG. 9 shows the jaw assembly in a partially closed condition.

The first jaw 121 has a pair of spaced-apart walls 124 (FIGS. 8A and 8B), and each wall defines a fixed, elongated slot 126 (FIG. 9). The second jaw 122 defines a downwardly depending central wall 127 in which is mounted a shaft 130 (FIG. 9). The opposite ends of the shaft 130 are received in one of the a slots 126 defined in each adjacent side wall 124 of the first jaw 121. The shaft 130 defines a pivot axis about which the second jaw 122 pivots relative to the first jaw 121. The shaft 130 can translate along the length of each slot 126 so that the proximal end of the second jaw 122 can move toward and away from the first jaw 121.

Figure 8A:
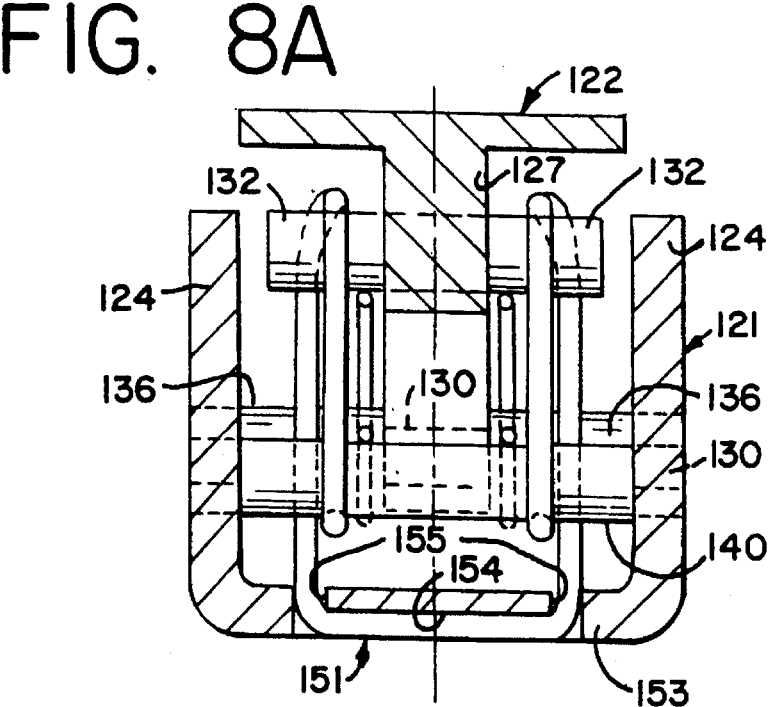
FIG. 8A is a cross-sectional view taken generally along plane 8A—8A in FIG. 8.

The central wall 127 of the second jaw 122 includes a first pin or roller 132 at a first location distally of said shaft 130, and the pin or roller 132 has two end portions projecting in opposite directions from the second jaw central wall 127 (FIG. 8A). Further, on each side of the second jaw central wall 127 there is a roller 136 mounted on the shaft 130.

The first jaw 121 defines a guide portion in the form of a fixed first pin 140 which extends between the first jaw walls 124. A second pin 142 (FIGS. 8–10) is mounted proximally of the slot 126 between the first jaw walls 124. Spaced above the second pin 142 is a third pin 144 which is also mounted between the walls 124 of the first jaw 121.

A pair of V-shaped springs 148 are provided in the jaw assembly to normally bias the second jaw 122 to an open position (as shown in FIG. 8). One spring 148 is mounted on one side of the second jaw central wall 127, and the other spring 148 is mounted on the other side of the central wall 127. Each spring 148 is mounted so that the interior angle at the apex of the V-shaped configuration of the spring receives the roller 136 on the shaft 130. The upper leg of each spring 148 is biased outwardly against the second jaw first roller or pin 132, and the end of the other leg of each spring is biased outwardly against the first jaw first pin 140. This arrangement tends to continuously bias the second jaw 122 toward the open position.

Figure 10:
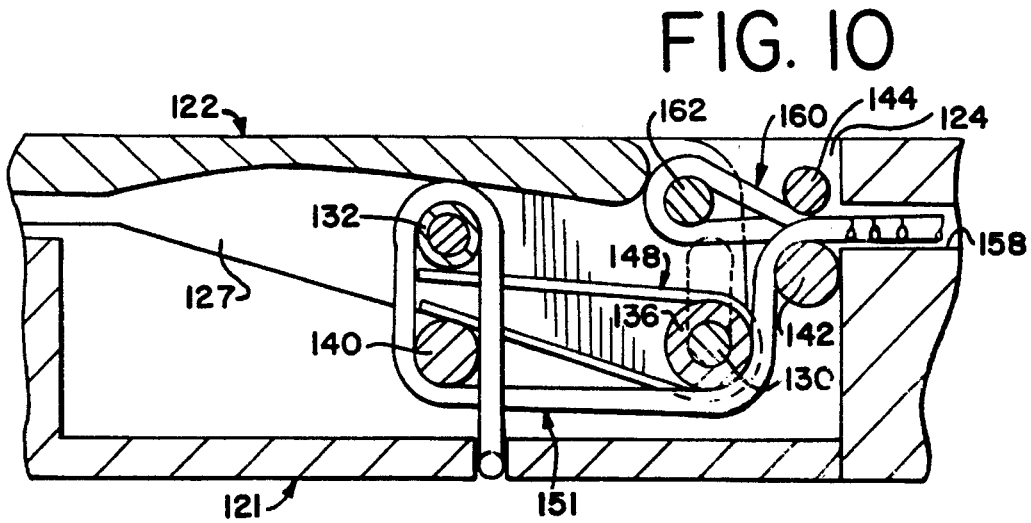
FIG. 10 is a view similar to FIG. 9, but FIG. 10 shows the jaw assembly in a fully closed condition.

The jaw assembly includes a first operating cord 151 which can be pulled from the proximal end of the instrument to pivot the second jaw 122 from the open position (FIG. 8) to the closed position (FIG. 10). In particular, the cord 151 has a generally U-shaped configuration around the first jaw 121 as illustrated in FIG. 8A. The first jaw 121 has a bottom wall 153 (FIG. 8A) which defines a transverse groove 154 and which defines two spaced-apart apertures 155 establishing communication between each end of the groove 154 and the interior of the first jaw 121.

The first cord 151 is seated within the groove 154, and portions of the cord 151 extend up through each aperture 155 on each side of the second jaw central wall 127. The cord is trained sequentially around the second jaw first roller 132, around the first jaw first pin 140, around the second jaw second roller 136, and finally around the first jaw second roller 142. The first cord 151 extends along both sides of the jaw assembly through an aperture 158 in the proximal portion of the first jaw 121. The two proximally extending lengths of the first cord 151 may then be routed to the proximal portion of the instrument to a location at which tension may be applied. The proximally extending lengths of the cord 151 can be joined together to form a continuous loop (FIG. 8B) and may be attached in the proximal portion of the instrument to an operating lever (e.g., similar to the lever 100 of the first embodiment of the jaw assembly described above with reference to FIG. 2). Alternatively, each proximally extending length of the cord 151 may be separately terminated at the proximal portion of the instrument to a lever or other device for pulling the cords proximally. The cord may even be manually grasped and pulled.

A second operating cord 160 is provided to pull on the proximal end of the second jaw 122. To this end, the proximal end of the second jaw 122 has a transversely projecting pin 162, and the second operating cord 160 is formed into a loop around the pin 162. The two lengths of the cord 160 extend proximally from the pin 162 between the first jaw pins 144 and 142 and through the first jaw aperture 158.

The proximally extending lengths of the second operating cord 160 extend to the proximal portion of the instrument along with the lengths of the first operating cord 151. As with the first operating cord 151, the second operating cord 160 is intended to be pulled or tensioned at the proximal end of the instrument by suitable means (not illustrated). The second operating cord 160 may be directly grasped and pulled or the second operating cord 160 may be engaged with a device operable by the surgeon for pulling the cord 160. The particular means for pulling the cord 160 form no part of the present invention.

Figure 8B:
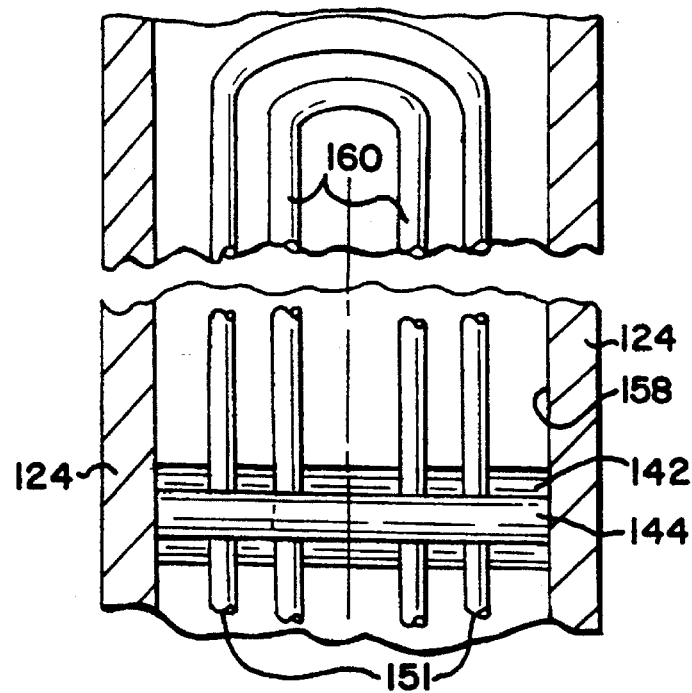
FIG. 8B is a fragmentary, cross-sectional view taken generally along the planes 8B—8B in FIG. 8.

The lengths of the second operating cord at the proximal end of the instrument may be joined together, as shown in FIG. 8B, so as to form a continuous loop. This permits engagement with a surgeon's finger, or with other mechanisms for pulling the loop, without the necessity of terminating separate cord end portions.

The first operating cord 151 and the second operating cord 160 may be provided in any of the 10 compositions and constructions that have been described above for the cord 96 in the first embodiment of the jaw assembly illustrated in FIGS. 1–7.

The jaw assembly illustrated in FIGS. 8, 8A, 8B, 9, and 10 may be operated to provide a loading bias relative to the distal end of the jaws which is proportional to the total closure force applied and to the amount of closure. The jaw assembly initially loads the distal end of the second jaw 122 with a fraction of the total closure force generated. Subsequently, the fraction of the total closure force increases as the second jaw 122 closes further and as the tissue reaction forces increase.

The initially open condition of the jaw assembly is established by pulling the second operating cord 160 to pivot the second jaw 122 upwardly relative to the first jaw 121. In this condition, the shaft 130 is urged against the bottom of the first jaw slots 126. The springs 148, acting between the first jaw pin 140 and the second jaw pin or roller 132, also force the jaws apart and insure that the first operating cable 151 is extended.

In order to initiate the closing of the jaws, the tension on the second operating cable 160 is released or partially released. The jaw opening springs 148 then move the proximal end of the first jaw 121 and the proximal end of the second jaw 122 further apart. This results in the second jaw shaft 130 moving upwardly to the upper end of the second jaw slots 126. The tension in the first operating cable 151 exerts an upward force on the shaft 130. As the tension in the first operating cable 151 is increased, the second jaw 122 pivots about the shaft 130 to lower the distal end of the second jaw 122 toward the first jaw 121 (FIG. 9).

Typically, tissue has been located between the jaws, and the distal end of the second jaw 122 engages the tissue and applies an increasing load or force on the tissue. As the tissue is compressed, the total reaction forces on the distal end of the second jaw 122 increase, and the first operating cord 151 must be pulled with increasingly greater force.

During a final closure portion of the jaw closing movement, the angle of the second jaw 122 relative to the first jaw 121 changes, and an increasing fraction of the total cable tension is transferred to the distal end of the second jaw 122. This permits the shaft 130 at the proximal end of the second jaw 122 to move downwardly in the slots 126 to provide a more uniform, final tissue compression. Because the tissue is initially compressed between the distal ends of the jaws and subsequently along an increasing length portion of each jaw, the tissue is not initially forced distally in the jaws. Thus, the tendency of the tissue to slip out of the jaws, as would be the case in a conventional pair of fixed pivot axis jaws, is eliminated or substantially minimized.

Figure 11:
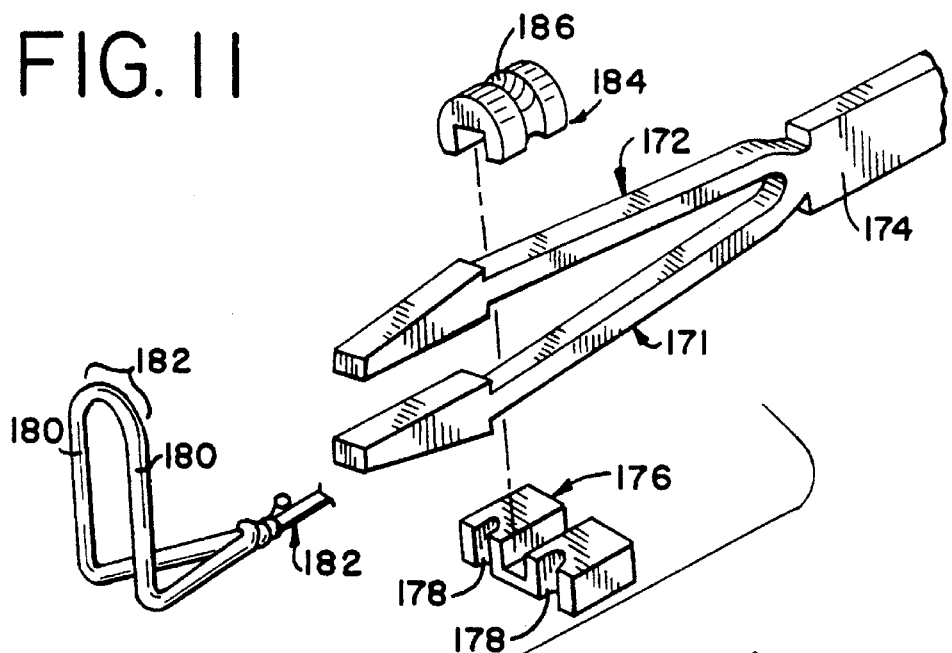
FIG. 11 is a fragmentary, exploded, perspective view of a third embodiment of a jaw assembly.
Figure 12:
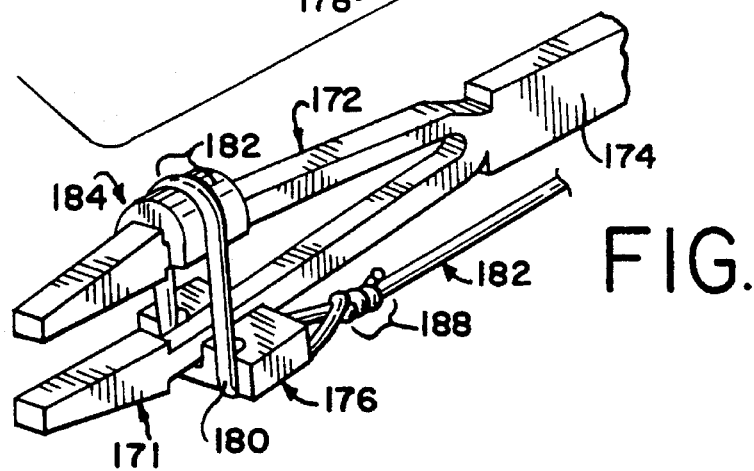
FIG. 12 is a fragmentary, perspective view of the jaw assembly of FIG. 11 shown in the assembled condition.

Another embodiment of the jaw assembly of the present invention is illustrated in FIGS. 11 and 12. The jaw assembly includes a first jaw 171 and a second jaw 172. Each jaw has a distal end. A proximal end of each jaw is connected to the proximal end of the other jaw to define a unitary structure that includes a base 174. Each jaw 171 and 172 is cantilevered from the base 174 and is resiliently deflectable toward the other. The jaw assembly functions as a spring structure for urging the two jaws apart to an open position.

The first jaw 171 includes a first bearing member 176 which defines a pair of spaced-apart, parallel grooves 178. Each groove defines a generally semi-cylindrical, lateral guide surface for receiving a portion 180 of a cord 182.

The second jaw 172 includes a saddle or second bearing member 184 defining a transverse, arcuate groove 186 for receiving an arcuate segment 188 of the cord 182. The arcuate segment 182 connects the cord portions 180.

The cord portions 180 and the connecting arcuate portion 182 define a U-shaped configuration which is engaged with the second jaw bearing member 184. The cord portions 180 may be characterized as trailing portions which each extend around the lateral guide surface defined by the first bearing member 176. The two portions 180 are joined together proximally of the bearing member 176, as at knot 188. The jaw assembly is thus relatively easy to fabricate and assemble.

When the cord 182 is pulled proximally, the jaws 171 and 172 close. This jaw assembly is especially suitable for use in closing ligating clips. The jaws can be closed with relatively high force, and the cable arrangement may be routed through an articulating instrument joint. Because the cord 182 can be engaged with the jaws relatively close to the distal ends of the jaws, the closure force is applied relatively close to the location where the forces are most needed—especially when deforming or crushing a ligating clip between the jaws.

Although the cord 182 is illustrated in FIGS. 11 and 12 as having a single, proximally extending portion, it will be appreciated that each of the portions 180 could extend separately along the jaw assembly and into the instrument. Such portions 180 could be connected to form a endless loop in the proximal end of the instrument (not shown) which could be attached or engaged with a suitable operating lever in the proximal portion of the instrument (e.g., similar to the connection of the loop cord 96 to the operating lever 100 in the first embodiment illustrated in FIG. 2).

Figure 13:
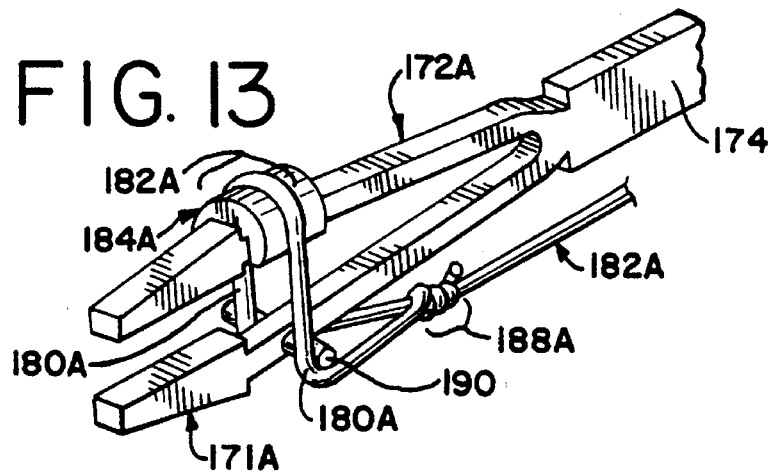
FIG. 13 is a view similar to FIG. 12, but FIG. 13 shows a fourth embodiment as modification of the jaw assembly illustrated in FIG. 12.

FIG. 13 illustrates a modification of the embodiment illustrated in FIGS. 11 and 12. The jaw assembly in FIG. 13 includes a unitary structure. This defining a first jaw 171A and a second jaw 172A. The jaw structure is substantially identical to the structure of the jaws 171 and 172 described above with reference to FIGS. 11 and 12. However, the first jaw 171A includes a laterally extending pin 190 in place of the member 176 illustrated in FIGS. 11 and 12. The pin 190 defines a lateral guide surface for engaging the trailing portions 180A of the cord 182A.

The cord portions 180A are connected with an arcuate section 182A which extends over a member or saddle 184A mounted on the second jaw 172A. The structure of the member 184A is substantially identical to the structure of the member 184 described above with reference to the embodiment illustrated in FIGS. 11 and 12. The cord portions 180A are connected proximally of the pin 190, as with the knot 188A. The jaw assembly illustrated in FIG. 13 is operated in substantially the same manner as the jaw assembly described above with reference to FIGS. 11 and 12.

Figure 14:
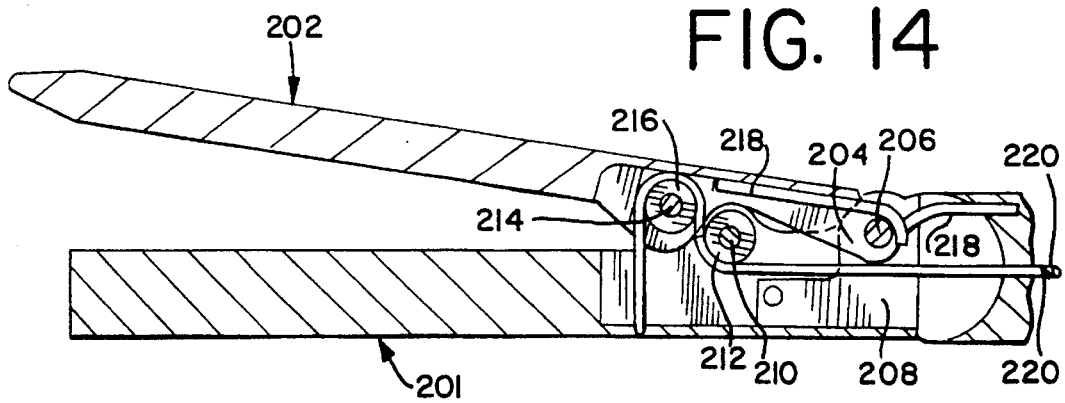
FIG. 14 is a fragmentary, cross-sectional view of a fifth embodiment of a jaw assembly in an open condition.
Figure 15:
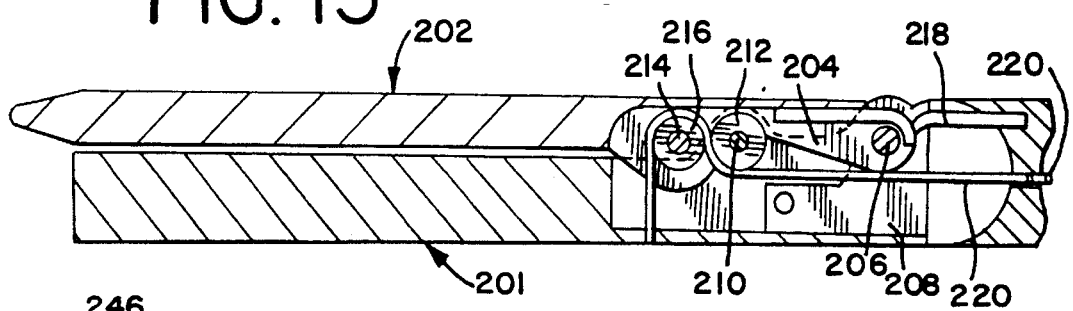
FIG. 15 is a view similar to FIG. 14, but FIG. 15 shows the jaw assembly in the closed condition.

Another embodiment of the jaw assembly of the present invention is illustrated in FIGS. 14 and 15. The jaw assembly has a first jaw 201 and a second jaw 202. Each jaw has a distal end and a proximal end. The jaws 201 and 202 are mounted together at their proximal ends. Specifically, the proximal end of the second jaw 202 has a pair of downwardly projecting, side walls 204. Only the far side wall 204 is visible in the figures. The walls 204 carry a pivot pin 206 that extends laterally beyond the walls 204. The proximal end of the first jaw 201 defines a pair of spaced-apart walls 208 exterior of the second jaw walls 204. The first jaw walls 208 which define suitable bores (not visible) for receiving the ends of the pivot pin 206.

A pin 210 is mounted to the walls of the first jaw 201 distally of the pivot pin 206. A roller 212 carried by the pin 210. The second jaw 202 also has a pin 214 mounted distally of the pivot pin 206 in the walls 204. A roller 216 is mounted on the pin 214.

A spring 218 is engaged with the first jaw 201 and with the second jaw 202 in a manner that normally biases the second jaw 202 upwardly to the open position illustrated in FIG. 14

An operating cord 220 is provided for closing the second jaw 202. The cord 220 is looped through the bottom of the lower jaw 201 in the same manner that the cord 151 is looped through the bottom 153 of the lower jaw 121 in FIG. 8A described above. The two trailing portions of the cord 220 extend proximally through the jaw assembly. Specifically, each trailing portion of the cord 220 is trained sequentially from the fixed portion around the roller 216 and then around the roller 212. The rollers 216 and 212 function as guide surfaces. When the cord 220 is tensioned, the second jaw 202 is pivoted to close relative to the first jaw 201 as illustrated in FIG. 15.

Figure 16:
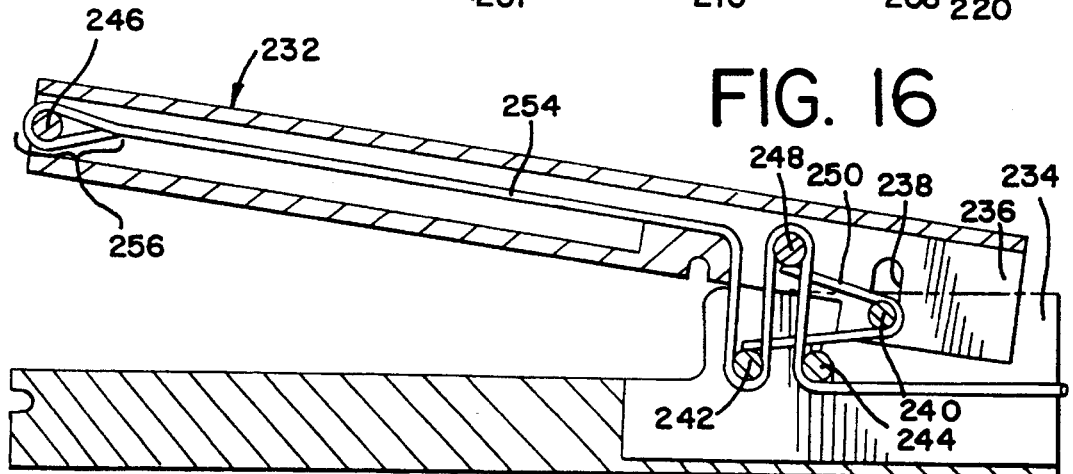
FIG. 16 is a fragmentary, cross-sectional view of a sixth embodiment of a jaw assembly.
Figure 17:
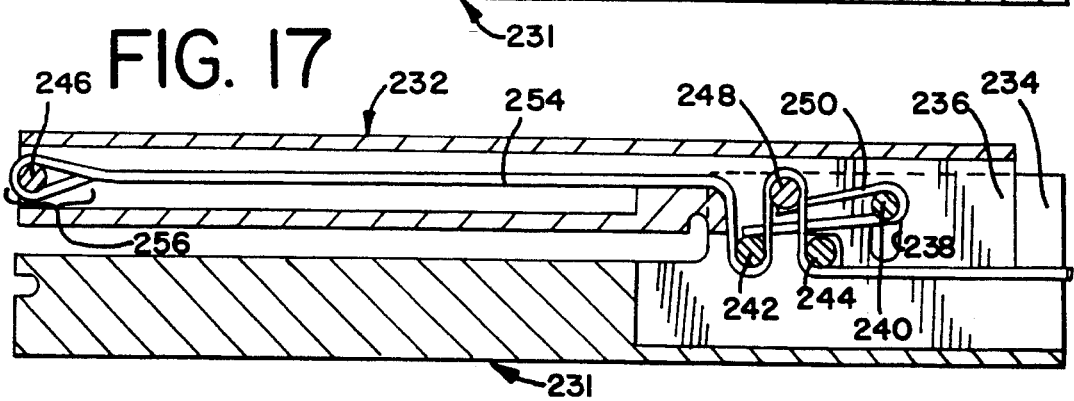
FIG. 17 is a view similar to FIG. 16, but FIG. 17 shows the jaw assembly in a closed condition.

Another embodiment of the jaw assembly present invention is illustrated in FIGS. 16 and 17. The jaw assembly includes a first jaw 231 having a distal end and proximal end, and the assembly includes a second jaw 232 having a distal end and a proximal end. The proximal end of the first jaw 231 defines a pair of side walls 234 (only the far side wall 234 being visible in FIGS. 16 and 17). The proximal end of the second jaw 232 is received between the first jaw side walls 234. The proximal end of the second jaw 232 also defines a pair of side walls 236 (only the far side wall 236 being visible in FIGS. 16 and 17).

The side walls 236 of the second jaw 232 each define an elongate slot 238 adjacent the proximal end. The first jaw 231 has a transversely extending shaft or pin 240 adjacent its proximal end and received in the elongate slots 238 for mounting the jaws together to accommodate translation and pivoting movement of the second jaw 232 toward and away from the first jaw 231.

The first jaw 231 has two spaced-apart guide surfaces or pins 242 and 244 extending between the spaced-apart walls 234 at the proximal end of the first jaw 231. The second jaw 232 has a pin 246 at its distal end extending between the second jaw side walls 236 and has another pin 248 which is located between the first pin 246 and the elongate slots 238 and which extends between the second jaw side walls 236.

A V-shaped spring 250 is mounted so that interior angle at the apex of the V-shaped configuration receives the pin 240. The upper leg of the spring 250 is biased outwardly against the second jaw first pin 248, and the lower leg of the spring 250 is biased outwardly against the first jaw pin 242. This arrangement continuously biases the second jaw 232 toward the open position.

An operating cord 254 is provided for closing the second jaw 232 relative to the first jaw 231. The cord 254 has a closed loop 256 at its distal end, and the second jaw distal end pin 246 is engaged by the loop 256. The operating cord 254 extends proximally in the second jaw 232 toward the proximal end of the second jaw 232.

At the proximal end of the second jaw 232, the cord 254 is trained around the first jaw pin 242, then around the second jaw pin 248, and then around the first jaw pin 244. The cord 254 extends proximally from the first jaw pin 244 into the proximal portion of the instrument (not shown) where it can be tensioned by suitable means (such as manually or with an operating lever that may be similar to the lever 100 of the first embodiment of the jaw assembly described above with reference to FIG. 2).

When the cord 254 is tensioned, the second jaw 232 is pivoted downwardly to the closed position illustrated in FIG. 17. When the tension on the cord 254 is released, the spring 254 urges the second jaw 232 to the open position illustrated in FIG. 16.

Alternatively, the cord 254 may be provided as a continuous (endless) loop around the second jaw distal end pin 246, and the trailing portions of the loop can extend together back to the proximal end around the pins 242, 248 and 244 in the same manner as the single cord length described above. Both trailing portions would be tensioned together to operate the jaw assembly.

Another embodiment of the jaw assembly of the present invention is illustrated in FIGS. 18, 18A, and 19. The jaw assembly includes a first jaw 261 having a distal end and a proximal end, and the assembly includes a second jaw 262 having a distal end and a proximal end. The proximal end of the first jaw 261 defines a pair of spaced-apart side walls 264 and 265.

The second jaw 262 has a pair of spaced-apart walls 266 and 267 projecting downwardly and received between the first jaw side walls 264 and 265. A pivot shaft or pin 268 is mounted in the second jaw side walls 266 and 267. One end of the pin 268 is received in an elongate slot 271 defined in the first jaw side wall 264, and the other end of the pin 268 is received in an elongate slot 272 defined in the first jaw side wall 265 (FIG. 18A). A roller 274 is disposed on the pin 268.

Located distally of the elongate slots 271 and 272 in the first jaw 261 is a pin 278 which extends between, and which is mounted at each end to, the side walls 264 and 265. A roller 280 is disposed on the pin 278.

Located proximally of the elongate slots 271 and 272 in the first jaw 261 are vertically spaced-apart pins 284 and 286. Each pin 284 and 286 extends between, and is mounted in, the first jaw walls 264 and 265. Spaced above the pin 284 is a transverse guide member 288 which extends between the first jaw walls 264 and 265.

A first operating cord 290 defines a loop around the jaws 261 and 262. In particular, the cord 290 has a bottom portion 292 engaged with the bottom of the first jaw 261. To this end, the bottom of the first jaw 261, and a portion of each side of the jaw 261, define a groove or channel 294 for receiving the cord 290 in a recessed relationship.

The cord 290 extends upwardly from the cord bottom portion 292 along each side of the jaw assembly, over the top of the second jaw 262 and back down along opposite sides of the second jaw 262. Preferably, a receiving channel or groove 296 is defined in the top and sides of the second jaw 262 for receiving the lengths of the cord 290.

Two portions of the cord 290 each extend downwardly along each side of the second jaw 262 from the top of the jaw 262 to the roller 280 carried on the first jaw 261. The portions of the cord 290 then extend proximally from the roller 280 between the first jaw side walls 264 and 265. The cord lengths 290 are engaged with the roller 274 on the pin 268 and then extend between the pins 284 and 268 proximally of the elongate slots 271 and 272. The lengths of the cord 290 extend through a suitable slot 300 in the first jaw 261 and further into the instrument where they may be tensioned manually or by suitable means. For example, the proximally extended lengths of the cord 290 can be joined together to form a continuous loop and may be attached in the proximal portion of the instrument to an operating lever (e.g., similar to the lever 100 of the first embodiment of the jaw assembly described above with reference to FIG. 2).

A second operating cord 302 is attached to the proximal end of the second jaw 262. To this end, the second jaw walls 266 and 267 carry a pin 306. The secondary operating cord 302 has a loop at its distal end engaged with the pin 306.

The cord is received between the guide member 288 and pin 284 in the first jaw 261, and the cord 302 extends proximally through a slot 308 in the proximal end of the first jaw 161.

The proximal end of the cord 302 may be formed into a loop (not illustrated) in the proximal portion of the instrument for being pulled manually or by means of a suitable lever or other mechanism.

Although not illustrated, it may be desirable in some applications to provide a spring similar to the spring 250 described above with reference to the embodiment illustrated in FIGS. 16 and 17. Such a spring would bias the second jaw 262 upwardly to the open position.

In operation, the second operating cord 302 can be initially tensioned to pull the proximal end of the second jaw 262 upwardly and rearwardly relative to the pivot pin 268. The pivot pin 268 is maintained at the upper ends of the elongate slots 271 and 272 in the open position. The jaw 262 can be maintained in this open position by maintaining tension on the second operating cord 302 even if a biasing spring is not employed to assist in opening the second jaw 262.

When it is desired to close the second jaw 262, tension is initially still maintained on the second operating cord 302. The tension is ultimately released gradually, and in a timed manner, as tension is applied to the first operating cord 290. However, initially, sufficient tension is maintained on the second operating cord 302 to keep the pin 268 in the elevated position in the slots 271 and 272 so that the distal end of the second jaw 262 engages the tissue between the jaws before the proximal portion of the first jaw 262 engages the tissue. In this respect, when the second jaw 262 has moved to an intermediate closed position, the second jaw 262 would be angled somewhat downwardly similar to the orientation shown for the jaw 122 in the second embodiment illustrated in FIG. 9.

As the tissue is compressed between the jaws, the total reaction forces on the second jaw 262 increase and the closing force required at the distal end of the second jaw 262 must increase to effect further closure. The clamping angle changes as the second jaw 262 closes further. This change in geometry results in an increasing fraction of the increasing tension in the first operating cable 290 being transferred to the distal end of the second jaw 262. The distal end of the second jaw 262 provides a tissue compression force which prevents the tissue from slipping out of the jaws as the jaws close.

The tension in the second operating cable 302 is gradually released to permit the proximal end of the second operating jaw 262 to move downwardly (under the increasing force applied by the first operating cable 290). The pin 268 thus moves downwardly to the bottoms of the slots 271 and 272, and the jaws may then assume a substantially parallel orientation with the tissue clamped between the jaws.

Figure 20:
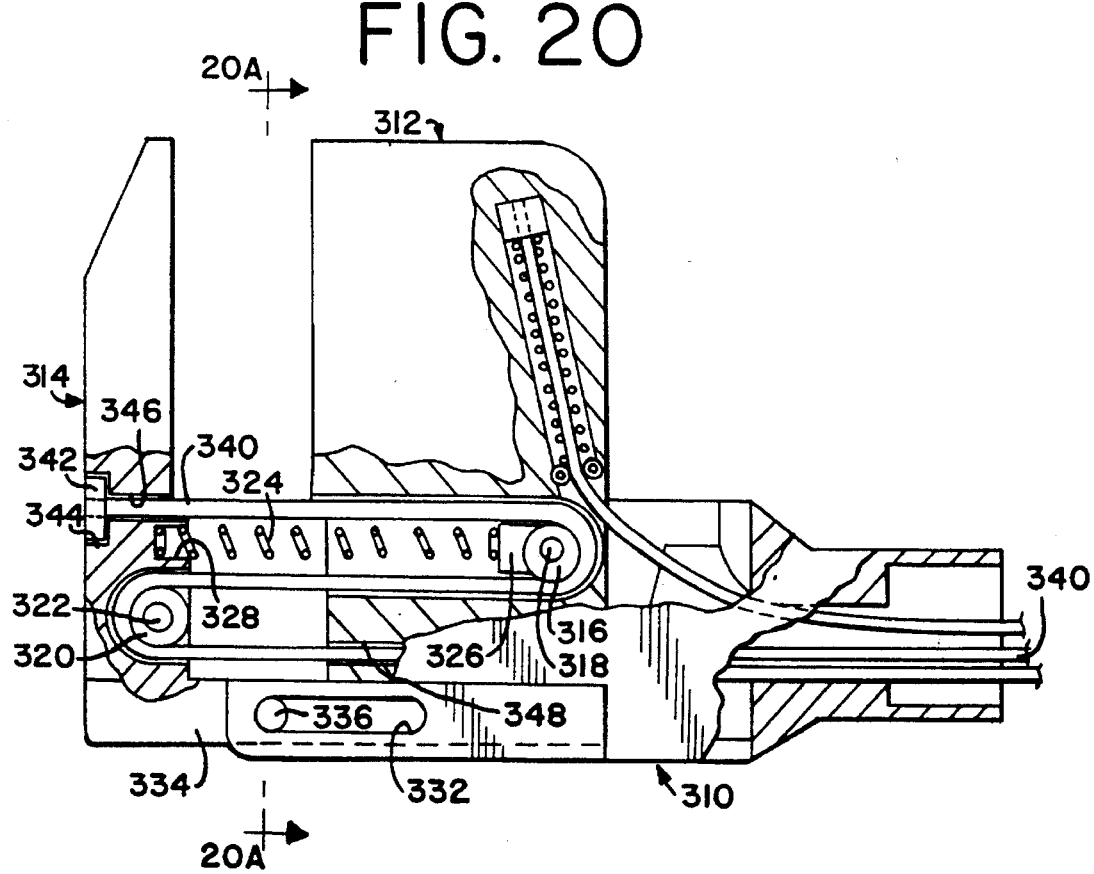
FIG. 20 is a fragmentary, side elevational view of an eighth embodiment of a jaw assembly with portions of the assembly broken away and shown in cross section to illustrate interior detail.
Figure 20A:
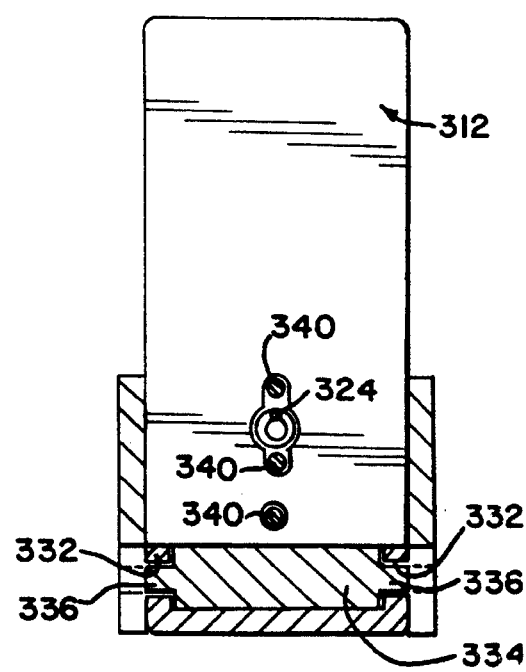
FIG. 20A is a cross-sectional view taken generally along the plane 20A—20A in FIG. 20.
Figure 20B:
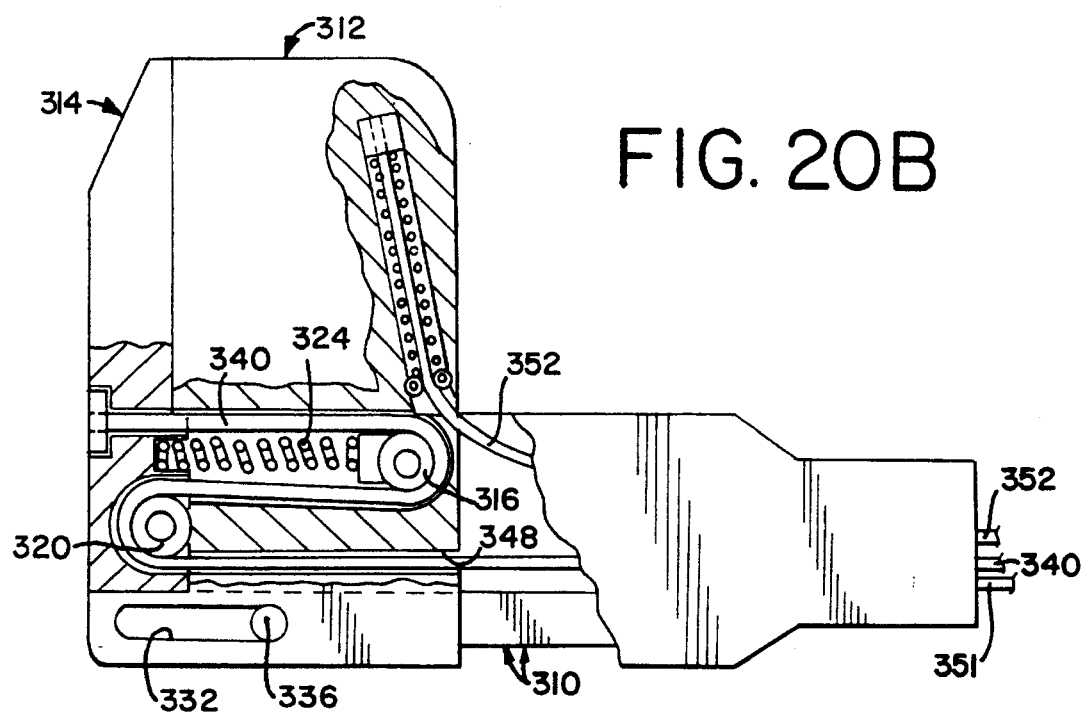
FIG. 20B is a view similar to FIG. 20 but shows the jaw assembly in a closed condition.

FIGS. 20, 20A, and 20B illustrate another embodiment of the jaw assembly of the present invention. The jaw assembly includes a frame 310 and a first jaw 312 projecting transversely from the frame 310. A second jaw 314 is carried on the frame 310 for moving toward and away from the first jaw 312 in an orientation generally fixed relative to the first jaw 310.

A first guide member is carried on the first jaw 312 or frame 310, and in the embodiment illustrated, the first guide member is a pulley 316 mounted for rotation on a shaft 318 carried in the stationary first jaw 312. A second guide member 320 in the form of a pulley is mounted on a shaft 322 carried in the second jaw 314.

The second jaw 314 is normally biased to an open position relative to the first jaw 312 by a compression spring 324. One end of the compression spring 324 bears against a block 326 in the first jaw 312, and the other end of the spring 324 is received in a recess 328 defined in the second jaw 314.

The frame 310 (or lower portion of the stationary first jaw 312) defines an elongate slot 332. The bottom of the second jaw 314 includes a proximally projecting foot 334 which carries a pair of oppositely projecting pins 336. Each pin 336 is received in one of the slots 332.

An operating cord 340 is connected to the second jaw 314. In particular, the distal end of the cord 340 is secured to an anchor disk 342 received in a recess 344 defined in the exterior, distal face of the second jaw 314. The cord 340 extends through a bore 346 in the second jaw 314, into the first jaw 312 and around the guide member or pulley 316.

The cord 340 extends from the guide member 316 back into the second jaw 314 and around the guide member or pulley 320 in the second jaw 314. The cord 340 then extends through a bore 348 in the first jaw 312 to the proximal end of the instrument. Suitable mechanisms (not illustrated) may be provided in the instrument for assisting in pulling on the cord 340 to effect closure of the jaws as illustrated in FIG. 20B.

The use of two pulleys 316 and 320 in the jaw assembly provides a 2 to 1 mechanical advantage for applying the closure force to the jaw assembly. Owing to the use of a flexible cord 340, the jaw assembly can be provided in an articulating instrument wherein the cord 340 can accommodate articulation of the jaw assembly relative to the rest of the instrument. To this end, a suitable, flexible cord 351 may extend from the instrument and connect to the jaw assembly for effecting articulation of the jaw assembly. The detailed design and operation of such an articulation system form no part of the present invention.

The jaw assembly illustrated in FIGS. 20, 20A, and 20B is particularly suitable for incorporating linear stapler components wherein staples are provided in a conventional or special cartridge (not illustrated). For example, a conventional cartridge of staples (not illustrated) can be held in the first jaw 312, and the staples can be applied to tissue between the jaws and deformed against the second jaw 314 which would act as an anvil. A suitable conventional or special staple cartridge firing system may be provided, and this can include an actuating cable 352. The incorporation of such a stapler system in the jaw assembly, and the detailed design and operation of such a stapler system, form no part of the present invention.

Figure 21:
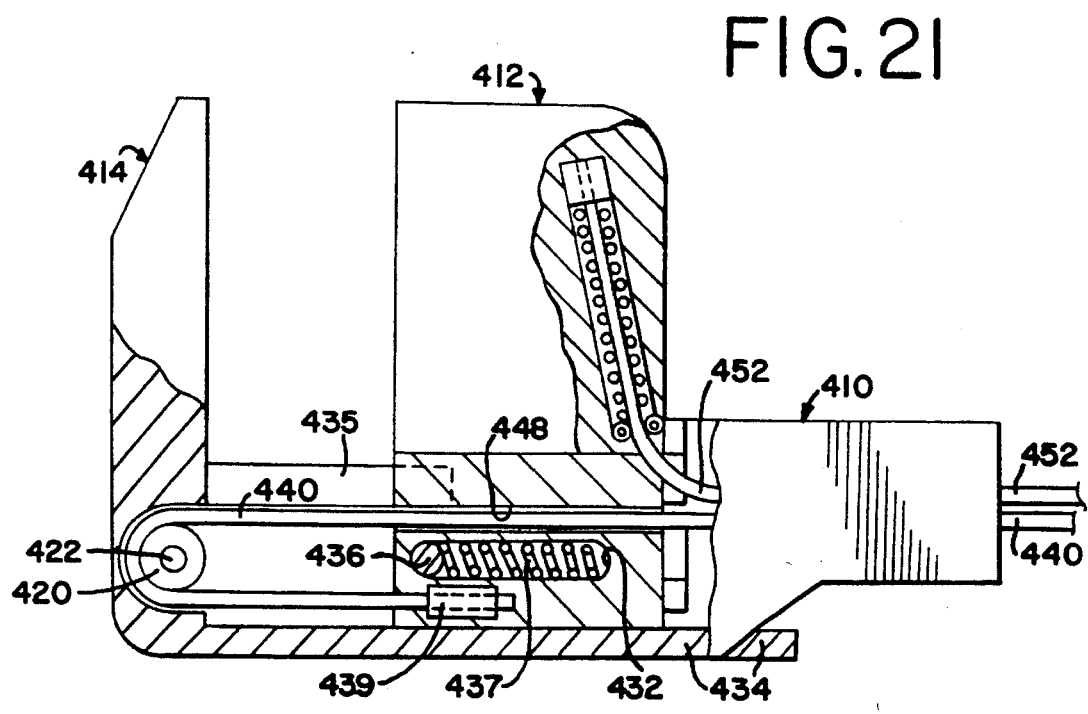
FIG. 21 is a fragmentary, side elevational view of a ninth embodiment of a jaw assembly with portions of the assembly cut away and shown in cross section to illustrate interior detail.

A modified jaw assembly somewhat similar to that illustrated in FIGS. 20, 20A and 20B is illustrated in FIG. 21. The assembly illustrated in FIG. 21 does not provide a 2 to 1 mechanical advantage, however. The jaw assembly includes a frame 410 and a first, stationary jaw 412. The first jaw 412 projects transversely from the frame 410.

A second jaw 414 is carried on the frame 410 for movement toward and away from the first jaw 412 in an orientation fixed relative to the first jaw 412. A guide member in the form of a pulley 420 is mounted on a pin 422 carried in the second jaw 414.

The first jaw 412 defines a slot 432. The second jaw 414 defines a foot 434 having a guide block 435 received in a cavity in the lower part of the first jaw 412. Pins 436 project laterally outwardly from the block 435. The pins 436 are disposed within slots 432 in the first jaw 412. A compression spring 437 is mounted in each slot to bias each pin 436, and hence the second jaw 414, distally to the open position illustrated in FIG. 21.

An operating cord 440 has a distal end connected to the stationary first jaw 412, as with a clamp bracket 439. The cord 440 is trained around the pulley 420 and extends through a bore 448 defined in the first jaw 412. The cord 440 extends to the proximal portion of the instrument where it may be engaged with a suitable operating mechanism or manually pulled so as to tension the cord and pull the second jaw 414 to a closed position against the first jaw 412. A linear stapling system, which may include an operating cord 452, may be provided in the jaw assembly as described above with reference to the embodiment illustrated in FIGS. 20, 20A, and 20B.

Further, if desired, the jaw assembly illustrated in FIG. 21 may be mounted so as to articulate on an instrument. The particular design and operation of such an articulating system form no part of the present invention.

Figure 22:
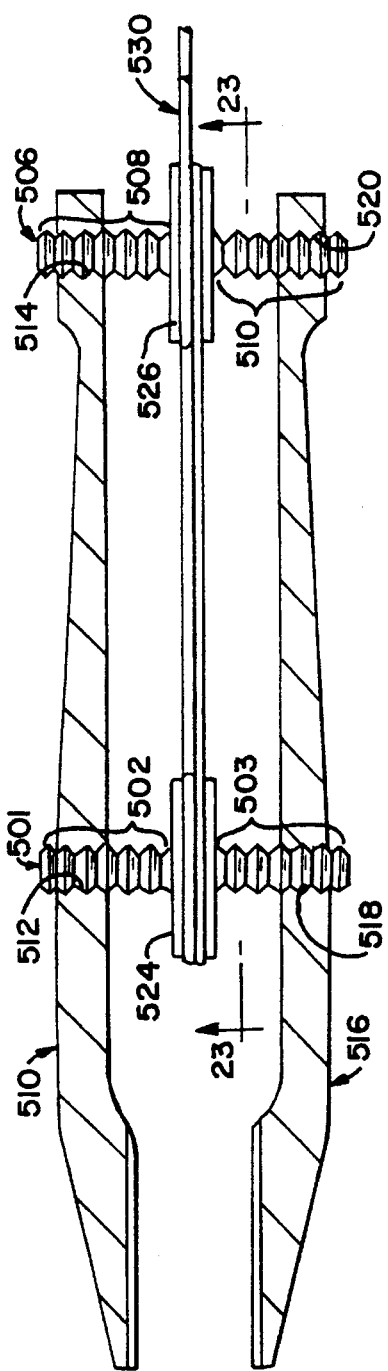
FIG. 22 is a fragmentary, cross-sectional plan view of a tenth embodiment of a jaw assembly.
Figure 23:
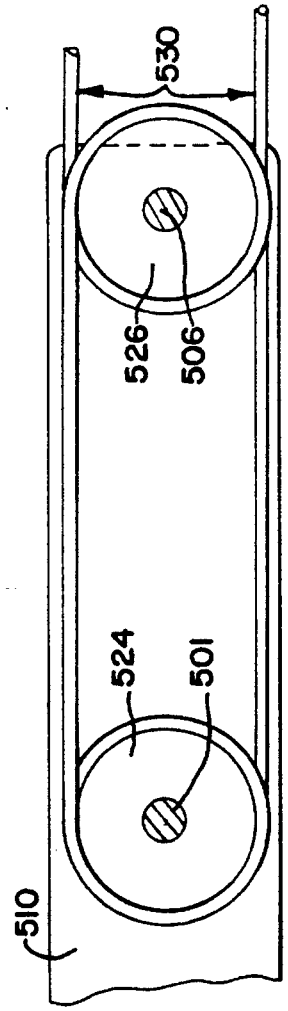
FIG. 23 is a fragmentary, cross-sectional view taken generally along the plane 23—23 in FIG. 22.
Figure 24:
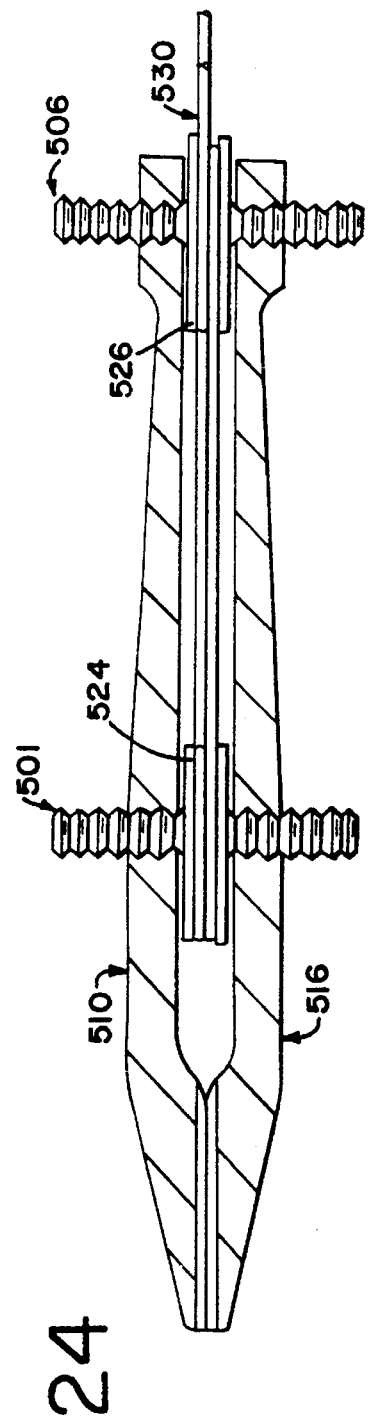
FIG. 24 is a view similar to FIG. 22, but FIG. 24 shows the jaw assembly in a closed condition.

Another embodiment of the jaw assembly of the present invention is illustrated in FIGS. 22–24. This embodiment of the jaw assembly effects closure of a pair of jaws in a substantially parallel relationship. The jaw assembly includes a first rod 501 having a first axial portion 502 defining a right-hand thread and having a second axial portion 503 defining a left-hand thread. Preferably, the jaw assembly also includes a second rod 506 having a first axial portion 508 defining a first right-hand thread and having a second axial portion 510 defining a left-hand thread. A first jaw 510 defines a first right-hand threaded bore 512 for receiving and threadingly engaging the first rod first axial portion 502. The first jaw 510 also defines a second right-hand threaded bore 514 for receiving and threadingly engaging the second rod second axial portion 508.

The assembly includes a second jaw 516. The second jaw 516 defines a first left-hand threaded bore 518 for receiving and threadingly engaging the first rod second axial portion 503. The second jaw 516 also defines a second left-hand threaded bore 520 for receiving and threadingly engaging the second rod second axial portion 509.

A first pulley 524 is mounted to the first rod 501 and fixed thereto. Similarly, a second pulley 526 is mounted to the second rod 506 and is fixed thereon. An operating cord 530 is trained around the first pulley, preferably 1½ times. Similarly, the operating cord 530 is trained around the second pulley 526 at least once.

Two portions of the cord 530 extend rearwardly into the proximal portion of the instrument (not illustrated) for being manipulated (manually or by a suitable operating device) to rotate the pulleys 524 and 526 together in one direction or the opposite direction. In one direction of rotation the jaws 510 and 516 will be moved together to the closed position (FIG. 24). In the opposite direction of rotation, the jaws will be moved apart to the open position (FIG. 22). If desired, a thin, cogged belt (not illustrated) could be disposed in the bottom of the pulleys 524 and 526 to insure synchronization of the pulleys and provide a better gripping surface.

This jaw assembly design provides a relatively simple construction and accommodates closure of the jaws in a substantially parallel manner with reduced clamping forces.

This jaw assembly design allows the use of high tensile cord and accommodates the use of the jaw assembly in an articulating instrument in which the jaw assembly can be articulated relative to the instrument while the flexible cord portions 530 accommodate the articulation.

If the jaw assembly is used in an articulating instrument, the proximal pulley rod 506 may be employed as an articulation pivot joint for the assembly. Then any cord sheaths and guides could be located proximally of the pulley 526 to save space and increase the potential articulation angle that could be accommodated.

Figure 25:
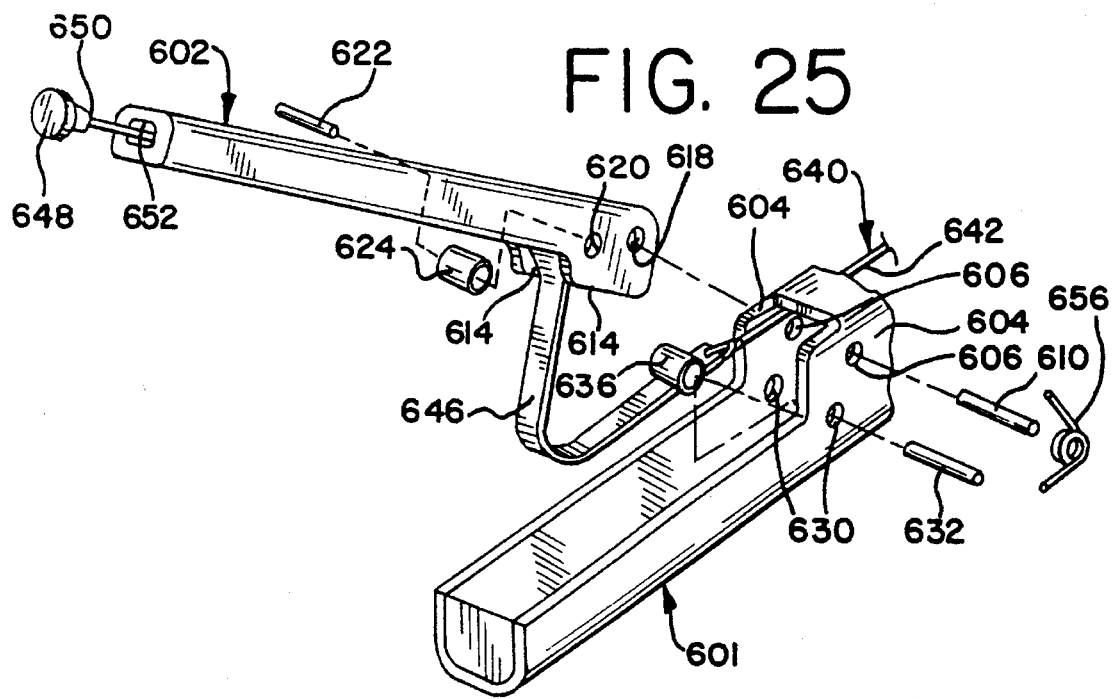
FIG. 25 is a fragmentary, exploded, perspective view of an eleventh embodiment of a jaw assembly.

FIG. 25 illustrates a further embodiment of the jaw assembly of the present invention. The assembly includes a first jaw 601 having a distal end and a proximal end, and a second jaw 602 having a distal end and a proximal end. The second jaw 602 is mounted for pivoting movement on the first jaw 601. To this end, the proximal end of the first jaw 601 includes a pair of spaced-apart walls 604 which each define a bore 606 for receiving a pivot pin 610. The proximal end of the second jaw 602 defines a pair of walls 614 which are spaced apart by an amount less than the spacing between the first jaw walls 604. The second jaw walls 614 are adapted to be received between the first jaw walls 604.

The second jaw wall 614 define bores 618 for receiving the pivot pin 610. The second jaw walls 614 also define another pair of bores 620 for receiving a pin 622. A roller 624 is disposed on the pin 622 between the walls 614.

The first jaw walls 604 define a pair of bores 630 for receiving a pin 632. A roller 636 is mounted on the pin 632.

An operating cord 640 is provided for operating the jaw assembly. The cord 640 includes a first portion in the form of a flexible, cylindrical filament 642. The cord 640 also includes a second, distal portion in the form of a flexible, metallic band 646. The distal end of the filament 642 is tied to, or otherwise attached to, the proximal end of the band 646. The band 646 extends along the length of the second jaw 602 and terminates in an anchor disc 648. The anchor disc 648 includes a plug 650 for being received in an aperture 652 defined at the distal end of the second jaw 602.

In the assembled condition, the filament 642 is positioned below the pivot pin 610. The proximal end of the metallic band 646 is positioned below the roller 636 carried on the first jaw 601. The band 646 has a generally Z-shaped configuration and is trained over the 10 roller 624 carried in the second jaw 602. Preferably, a torsion spring 656 is mounted on the pin 610 to normally urge the second jaw 602 to pivot upwardly to carry the distal end of the second jaw 602 away from the first jaw 601.

The jaw assembly can be closed by pulling on the filament 642 from the proximal portion of the instrument. Suitable mechanisms (not illustrated) may be provided for engaging the proximal portion of the filament 642 in the proximal portion of the instrument. For example, this could include an operating lever similar to the lever 100 of the first embodiment of the jaw assembly described above with reference to FIG. 2.

Figure 26:
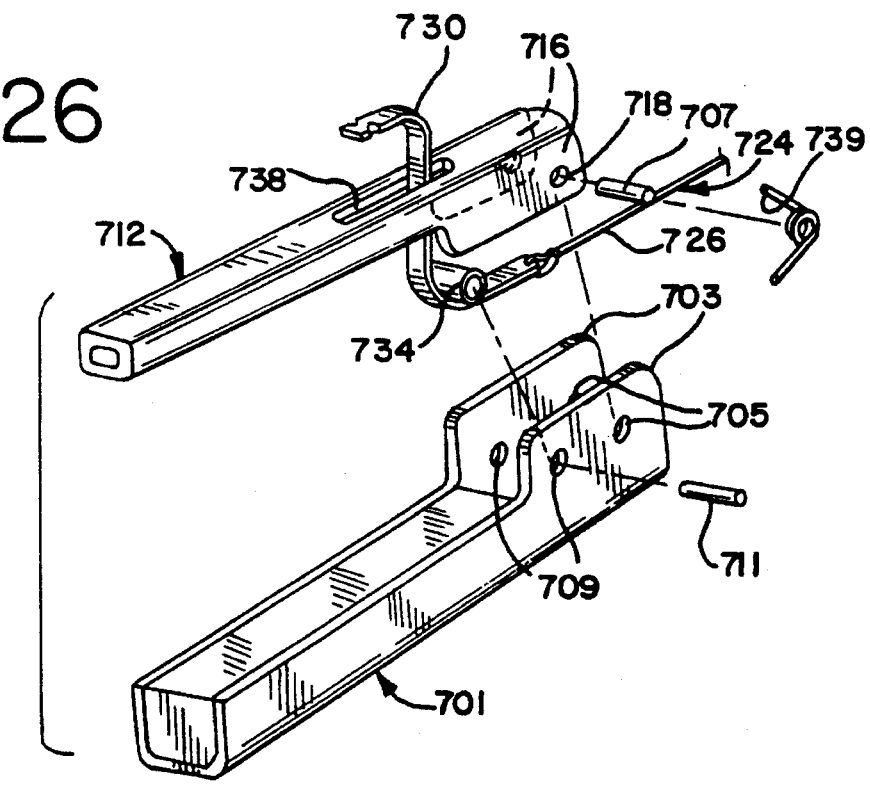
FIG. 26 is an exploded, perspective view of a twelfth embodiment of a jaw assembly.

FIG. 26 illustrates another embodiment of the jaw assembly of the present invention. The jaw assembly includes a first jaw 701 having a distal end and having a proximal end defining a pair of spaced-apart walls 703. The walls 703 define a first pair of aligned apertures 705 for receiving a pivot pin 707. The walls 703 define a second pair of apertures 709 for receiving another pin 711.

A second jaw 712 has a distal end and has a proximal end which is pivotally mounted to the proximal end of the first jaw 701. To this end, the proximal end of the second jaw 712 includes a pair of walls 716 for being received between the first jaw walls 703. The second jaw walls 716 also define a pair of bores 718 for receiving the pivot pin 707.

An operating cord 724 is provided for operating the jaw assembly. The operating cord 724 includes a proximal portion in the form of a thin, cylindrical, flexible filament 726 and a distal portion in the form of a flexible, metallic band 730. The distal end of the filament 726 is tied to, or otherwise secured to, the proximal end of the band 730. The filament 726 and band 730 are disposed under the pivot pin 707 and under the other pin 711. Preferably, a roller 734 is disposed on the pin 711 for contacting the band 730.

The distal end of the band 730 is secured by suitable means to the second jaw 712. In one contemplated form of connection, the second jaw 712 defines a slot 738 into which a distal end portion of the band 730 is disposed and held by means of an insert wedge (not illustrated).

Preferably, the band 730 has a generally Z-shaped configuration. A spring, such as a torsion spring 739, can be provided to normally urge the second jaw 712 to an open position. The jaw 712 can be closed by pulling on the filament 724 from the proximal portion of the instrument.

FIGS. 27–30 illustrate another embodiment of jaw assembly of the present invention. The assembly includes a first jaw 801 having a distal end and a proximal end, and includes a second jaw 802 having a distal end and a proximal end. The proximal end of the first jaw 801 includes a pair of side walls 804 (FIG. 30). Each wall 804 defines an elongate slot 806.

The first jaw 801 also includes a first guide pin 808 located distally of the slots 806 and extending between the walls 804. A pair of spaced-apart sleeves or rollers 810 are disposed on the pin 808 (FIGS. 27 and 30).

A second guide pin 814 is located proximally of the slots 806 in the first jaw 801. The second guide pin 814 extends between the first jaw walls 804. A roller or sleeve 816 is mounted on the pin 814.

Finally, an upper pin 818 is mounted between the first jaw walls 804 above the pin 814.

The second jaw 802 includes a pair of side walls 822. The walls 822 are spaced-apart by an amount that is less than the spacing between the first jaw walls 804. Mounted between the second jaw side walls 822 is a pivot pin 824. The distal ends of the pin 824 extend into the slots 806 in the side walls 804 of the first jaw 801. Two sleeves or rollers 826 are mounted on the pin between the second jaw walls 822. The rollers 826 are spaced apart at the center.

The second jaw 802 includes a third guide pin 830 located distally of the slots 806 and extending between the second jaw walls 822. Two sleeves or rollers 832 are disposed on the pin 830. The rollers 832 are spaced apart at the middle of the pin 830.

A V-shaped spring 840 is mounted between the first jaw 801 and second jaw 802. The spring 840 is mounted so that the interior angle at the apex of the V-shaped configuration of the spring receives the pivot shaft 824 between the spaced-apart rollers 826.

The upper leg of the spring 840 is biased outwardly against the second jaw guide pin 830 between the two spaced-apart rollers 832. The end of the other leg of the spring 840 is biased outwardly against the first jaw guide pin 808 between the two spaced-apart rollers 810. This arrangement tends to continuously bias the second jaw 802 toward the open position (FIGS. 27 and 30).

A first operating cord 850 has two portions or lengths extending into the proximal end of the first jaw 801, one length on each side of the spring 840. Each length has a first portion extending between the pin 814 and pivot shaft 824. Each first portion of the cord 850 engages the roller 816 on the pin 814 and the roller 826 on the pivot shaft 824.

Each portion of the cord 850 extends distally from the pivot shaft 824 and sequentially around the guide pin 808 on the first jaw 801 and then around the guide pin 830 on the second jaw 802. The cord engages the roller 810 on the pin 808 and engages the roller 832 on the pin 830.

The cord extends from the guide pin 830 on the second jaw 802 down to the bottom of the first jaw 801 on each side of the spring 840. To this end, the bottom of the jaw 801 define two spaced-apart bores 856 (FIG. 30) to accommodate passage of a portion of the cord 850. As shown in FIG. 30, the downwardly extending portions of the cord 850 define a common horizontal portion 858 below the first jaw 801. As viewed in FIG. 30, the portions of the cord 850 in the bottom of the first jaw 801 define a generally U-shaped configuration around a bottom portion of the first jaw 801.

The portions of the operating cord 850 extending proximally of the jaw assembly can be joined together to form a continuous loop and may be attached in the proximal portion of the instrument (not illustrated) to an operating lever (e.g., similar to the lever 100 of the first embodiment of the jaw assembly described above with reference to FIG. 2).

A second operating cord 860 is connected to the second jaw 802. Specifically, the proximal end of the second jaw 802 includes a pin 862 extending between the walls 822. The second operating cord 860 is looped around the pin 862 and extends to the proximal portion of the instrument (not illustrated). The proximally extending lengths of the second operating cord 860 may be joined together to form a continuous loop and may be attached in the proximal portion of the instrument to an operating lever (e.g., similar to the lever 100 of the first embodiment of the jaw assembly described above with reference to FIG.2).

The second jaw 802 can be maintained in the maximum open position as illustrated in FIG. 27 by maintaining tension on the second operating cord 860. This ensures that the pivot shaft 824 is at the top of the slots 806 in the first jaw 801 and that the second jaw 802 is pivoted in a clockwise direction as viewed in FIG. 27 to a fully opened position.

When it is desired to close the jaw assembly, tension is applied to the first operating cord 850. Initially, sufficient tension is also maintained on the second operating cord 860 to hold the pivot shaft 824 in the elevated position in the slots 806. In a nearly closed position, the distal end of the second jaw 802 will be angled downwardly near the first jaw 801 as shown in FIG. 28. The proximal end of the second jaw 802 remains elevated owing to the continued application of tension to the second operating cord 860.

Because the distal end of the second jaw 802 engages the tissue on the first jaw 801 prior to the proximal portion of the second jaw 802 engaging the tissue, the tissue is initially clamped near the distal end of the jaws and prevented from being forced outwardly along the jaws.

When the tissue has been sufficiently compressed by the downwardly angled, distal end of the second jaw 802, the tension in the second operating cord 860 is gradually released while the tension on the first operating cord 850 is maintained or increased. This procedure may be effected in response to tactile sensation or visual observation. This process may also be effected by suitable devices for automatically timing the release of tension in the second operating cord 860.

When sufficient tension has been released in the second operating cord 860, the proximal end of the second jaw is pulled downwardly owing to the tension in the first operating cord 850. The pivot shaft 824 moves to the bottom of the slots 806 in the first jaw 801. The second jaw 802 can then assume a substantially parallel orientation relative to the first jaw 801.

In the above-described embodiments, the cords, or portions of the cords, are preferably made from materials which are non-toxic and which have good physical, chemical, radiological, and biological characteristics. Some of the materials that may be used are the cobalt sterilizable, non-toxic, liquid-crystal, polyester-polyarylate polymer materials sold in the United States of America under the tradenames VECTRAN and VECTRA by Hoechst Celanese which has an office in Bridgewater, N.J., U.S.A. These materials also appear to exhibit a strength, resistance to creep, and thermal expansion coefficient which are especially suitable for use in surgical instruments.

It will be readily apparent from the foregoing detailed description of the invention and from the illustrations thereof that numerous other variations and modifications may be effected without departing from the true spirit and scope of the novel concepts or principles of this invention.

What is claimed is:

1. A jaw assembly for a surgical instrument, said assembly comprising:

a first jaw;

a movable second jaw having a jaw pivot axis and mounted for pivoting movement about said jaw pivot axis toward and away from said first jaw;

a lever mounted for pivoting movement about a lever pivot axis fixed relative to said first jaw, said lever defining first and second surfaces, the distance between said lever pivot axis and any part of said first surface being less than the distance between said lever pivot axis and any part of said second surface;

an operating cord engaged with said second jaw and engaged with said lever first and second surfaces for pulling said second jaw to pivot toward said first jaw;

in which said cord defines a generally U-shaped configuration around said second jaw; and said cord includes two trailing portions which each extend along opposite sides of said jaw assembly from said lever.

2. A jaw assembly for a surgical instrument, said assembly comprising:

a first jaw;

a movable second jaw having a jaw pivot axis and mounted for pivoting movement about said jaw pivot axis toward and away from said first jaw;

a lever mounted for pivoting movement about a lever pivot axis fixed relative to said first jaw, said lever defining first and second surfaces, the distance between said lever pivot axis and any part of said first surface being less than the distance between said lever pivot axis and any part of said second surface;

an operating cord engaged with said second jaw and engaged with said lever first and second surfaces for pulling said second jaw to pivot toward said first jaw;

in which said jaw assembly includes at least one wall defining a fixed elongate slot;

said second jaw has a proximal end and a distal end;

said second jaw is mounted on a shaft that is located adjacent said proximal end and that defines said jaw pivot axis; and said shaft is disposed in said slot to accommodate movement of said second jaw proximal end toward and away from said first jaw.

3. The jaw assembly in accordance with claim 2 in which said one wall is defined by said first jaw.

4. The jaw assembly in accordance with claim 2 in which said first jaw defines two of said walls in a spaced-apart configuration with each wall defining one of said fixed elongate slots; and said shaft is received in both of said slots whereby said second jaw is carried on said first jaw.

5. The jaw assembly in accordance with claim 4 further including a spring biasing said second jaw relative to said first jaw to urge said second jaw shafts toward one end of each said slot.

6. A jaw assembly for a surgical instrument, said assembly comprising:

a first jaw;

a movable second jaw having a jaw pivot axis and mounted for pivoting movement about said jaw pivot axis toward and away from said first jaw;

a lever mounted for pivoting movement about a lever pivot axis fixed relative to said first jaw, said lever defining first and second surfaces, the distance between said lever pivot axis and any part of said first surface being less than the distance between said lever pivot axis and any part of said second surface;

an operating cord engaged with said second jaw and engaged with said lever first and second surfaces for pulling said second jaw to pivot toward said first jaw;

in which said second jaw has a distal end; and said cord is engaged with said second jaw between said second jaw pivot axis and said distal end.

7. A jaw assembly for a surgical instrument, said assembly comprising:

a first jaw;

a movable second jaw having a jaw pivot axis and mounted for pivoting movement about said jaw pivot axis toward and away from said first jaw;

a lever mounted for pivoting movement about a lever pivot axis fixed relative to said first jaw, said lever defining first and second surfaces the distance between said lever pivot axis and any part of said first surface being less than the distance between said lever pivot axis and any part of said second surface;

an operating cord engaged with said second jaw and engaged with said lever first and second surfaces for pulling said second jaw to pivot toward said first jaw; and in which said cord defines a closed loop.

8. A jaw assembly for a surgical instrument, said assembly comprising:

a first jaw having a distal end and a proximal end;

a movable second jaw having a distal end and a proximal end, one of said jaws defining an elongate slot adjacent its proximal end, and the other of said jaws having a transversely extending shaft adjacent its proximal end and received in said slot for mounting said jaws together to accommodate translation and pivoting movement of said second jaw toward and away from said first jaw;

a spring biasing said second jaw relative to said first jaw for urging said second jaw to pivot away from said first jaw; and a first operating cord engaged with said second jaw at a first location distally of said shaft for pulling said second jaw to pivot said second jaw distal end toward said first jaw, said first operating cord also being engaged with said second jaw at a second location proximally of said first location for urging said second jaw proximal end away from said first jaw only during an initial portion of the pivoting movement of said second jaw distal end toward said first jaw.

9. The jaw assembly in accordance with claim 8 further including a second operating cord engaged with said second jaw proximal end whereby pulling said second cord urges said second jaw proximal end toward said first jaw with concomitant relative displacement between said shaft and said slot.

10. The jaw assembly in accordance with claim 8 in which said cord defines a generally U-shaped configuration around a portion said first jaw; and said cord includes two trailing portions which each extend along opposite sides of said jaw assembly.

11. The jaw assembly in accordance with claim 8 in which said cord defines a closed loop.

12. The jaw assembly in accordance with claim 8 in which said shaft is carried on said second jaw and said slot is defined in said first jaw.

13. A jaw assembly for a surgical instrument, said assembly comprising:

first and second jaws with at least one of said jaws movable toward the other;

a spring structure for urging said jaws apart;

said first jaw having a lateral guide surface;

an operating cord defining a U-shaped loop configuration engaged with said second jaw and having at least one trailing portion extending around said lateral guide surface whereby said trailing portion can be pulled to urge at least one of said jaws toward the other of said jaws.

14. The jaw assembly in accordance with claim 13 in which said cord defines a generally U-shaped loop configuration around said second jaw with two trailing portions extending on opposite sides of said first jaw and joined together to define a closed loop.

15. The jaw assembly in accordance with claim 13 in which said second jaw includes a transverse guide surface; and said cord engages said transverse guide surface.

16. The jaw assembly in accordance with claim 13 in which said first jaw includes a first bearing member defining a pair of spaced-apart, parallel grooves, at least one of said parallel grooves defining said lateral guide surface for receiving said one trailing portion of said cord; and said second jaw includes a second bearing member defining a transverse, arcuate groove for receiving said cord.

17. A jaw assembly for a surgical instrument, said assembly comprising:

a first jaw and a first guide surface fixed relative to said first jaw;

a movable second jaw having a second guide surface and mounted for pivoting movement toward and away from said first jaw;

a spring biasing said second jaw relative to said first jaw for urging said second jaw to pivot away from said first jaw; and a cord having a portion fixed relative to said first jaw and having a trailing portion trained sequentially from said fixed portion around said second guide surface and then around said first guide surface for pulling said second jaw to pivot toward said first jaw.

18. The jaw assembly in accordance with claim 17 in which said jaw assembly includes a pivot shaft defining a pivot axis;

said second jaw has a proximal end and a distal end; and said second jaw is mounted for pivoting movement about said axis adjacent said proximal end.

19. A jaw assembly for a surgical instrument, said assembly comprising:

a first jaw having a distal end and a proximal end;

a movable second jaw having a distal end and a proximal end, one of said jaws defining an elongate slot adjacent its proximal end, and the other of said jaws having a transversely extending shaft adjacent its proximal end and received in said slot for mounting said jaws together to accommodate translation and pivoting movement of said second jaw toward and away from said first jaw;

a spring biasing said second jaw relative to said first jaw for urging said second jaw proximal end to translate away from said first jaw and to urge said second jaw distal end to pivot away from said first jaw; and an operating cord connected with said second jaw at a first location distally of said shaft for pulling said second jaw to pivot said second jaw distal end toward said first jaw, said operating cord also being engaged with said second jaw at a second location proximally of said first location for urging said second jaw proximal end toward said first jaw as said second jaw distal end moves toward said first jaw.

20. The jaw assembly in accordance with claim 19 in which said second jaw includes a wall defining said slot; and said shaft is carried on said first jaw.

21. The jaw assembly in accordance with claim 19 in which said first jaw has two spaced-apart guide surfaces;

said second jaw has one guide member defining said second location; and said cord extends from said first location and is trained sequentially around one of said first jaw guide surfaces, around said second jaw guide member, and then around the other of said first jaw guide surfaces.

22. A jaw assembly for a surgical instrument, said assembly comprising:

a frame;

a first jaw projecting transversely from said frame;

a second jaw carried on said frame for movement toward and away from said first jaw in an orientation fixed relative to said first jaw;

a first guide member carried on one of said first jaw and frame;

a second guide member carried on said second jaw;

a slot defined by one of said frame and second jaw;

a guide pin carried on the other of said frame and second jaw and received in said slot to accommodate movement of said second jaw;

a spring biasing said second jaw away from said first jaw; and a cord that is connected to said second jaw, said cord being trained sequentially from said first jaw around said first guide member and then around said second guide member, said cord extending from said second guide member proximally of said jaw assembly whereby the pulling of said cord effects the closure of said jaws.

23. A jaw assembly for a surgical instrument, said assembly comprising:

a frame;

a first jaw projecting transversely from said frame;

a second jaw carried on said frame for movement toward and away from said first jaw in an orientation fixed relative to said first jaw;

a guide member carried on one of said first jaw and frame;

a slot defined by one of said frame and second jaw;

a pin carried on the other of said frame and second jaw and received in said slot to accommodate movement of said second jaw;

a spring biasing said second jaw away from said first jaw; and a cord that is connected to said second jaw, that extends around said guide member, and that extends proximally of said jaw assembly whereby the pulling of said cord effects the closure of said jaws.

24. A jaw assembly for a surgical instrument, said assembly comprising:

a first jaw having a distal end and a proximal end;

a movable second jaw having a distal end and a proximal end, one of said jaws defining an elongate slot adjacent its proximal end, and the other of said jaws having a transversely extending shaft adjacent its proximal end and received in said slot for mounting said jaws together to accommodate translation and pivoting movement of said second jaw toward and away from said first jaw;

said first jaw having a first guide pin located distally of said slot and a second guide pin located proximally of said slot;

said second jaw having a third guide pin located distally of said slot;

a spring biasing said second jaw relative to said first jaw for urging said second jaw to pivot relative to said first jaw;

a first operating cord having at least a first portion extending into said first jaw from the proximal end of said first jaw, said cord first portion extending between, and engaging, said first jaw second guide pin and said shaft, said cord first portion extending distally from said shaft and sequentially around said first guide pin on said first jaw and then around said third guide pin on said second jaw, said cord first portion extending from said third guide pin on said second jaw to, and engaged with, said first jaw at a location spaced from said first guide pin; and a second operating cord connected to said second jaw proximal end whereby applying tension said second cord prevents said second jaw proximal end from moving toward said first jaw.

25. The jaw assembly in accordance with claim 24 in which said first operating cord includes a second portion spaced from, and generally parallel to, said second portion to extend into said first jaw from the proximal end of said first jaw, said cord second portion extending between, and engaging, said first jaw second guide pin and said shaft, said cord second portion extending distally from said shaft and sequentially around said first guide pin on said first jaw and then around said third guide pin on said second jaw, said cord second portion extending from said third guide pin on said second jaw to, and engaged with, said first jaw at a location spaced from said first guide pin; and said first operating cord first and second portions define a generally U-shaped configuration around part of said first jaw at said location spaced from said guide pin.

26. The jaw assembly in accordance with claim 24 in which said cord defines a closed loop.

27. The jaw assembly in accordance with claim 24 in which said shaft is carried on said second jaw and said slot is defined in said first jaw.

28. A jaw assembly for a surgical instrument, said assembly comprising:

a first jaw having a distal end and a proximal end;

a movable second jaw having a distal end and a proximal end, said second jaw being mounted for pivoting movement about a pivot axis toward and away from said first jaw;

a first operating cord engaged with said second jaw distally of said pivot axis for pulling said second jaw to pivot the distal end of said second jaw toward said first jaw; and a second operating cord engaged with said second jaw and arranged to pull said second jaw proximal end away from said first jaw when said second operating cord is tensioned.

* * * * *